US009814456B2

(12) United States Patent
Deitch et al.

(10) Patent No.: US 9,814,456 B2
(45) Date of Patent: Nov. 14, 2017

(54) TOOL USEFUL FOR IMPLANTING A SUPPORT IN TREATING URINARY INCONTINENCE IN A PATIENT

(71) Applicant: Coloplast A/S, Humlebaek (DK)

(72) Inventors: Sarah J. Deitch, Minneapolis, MN (US); Rachael Anne Bergstrom Crabb, St. Paul, MN (US); Mark A. Moschel, Plymouth, MN (US); Michael M. Witzmann, Shoreview, MN (US)

(73) Assignee: Coloplast A/S, Humlebaek (DK)

( * ) Notice: Subject to any disclaimer, the term of this patent is extended or adjusted under 35 U.S.C. 154(b) by 37 days.

(21) Appl. No.: 14/968,905

(22) Filed: Dec. 15, 2015

(65) Prior Publication Data

US 2016/0095587 A1  Apr. 7, 2016

Related U.S. Application Data

(63) Continuation of application No. 14/050,367, filed on Oct. 10, 2013, now Pat. No. 9,241,779.

(60) Provisional application No. 61/884,145, filed on Sep. 30, 2013, provisional application No. 61/721,563, filed on Nov. 2, 2012.

(51) Int. Cl.
*A61B 17/04* (2006.01)
*A61F 2/00* (2006.01)
*A61B 17/06* (2006.01)
*A61B 17/00* (2006.01)
*A61B 90/00* (2016.01)

(52) U.S. Cl.
CPC ........ *A61B 17/0401* (2013.01); *A61F 2/0045* (2013.01); *A61B 17/06109* (2013.01); *A61B 2017/00805* (2013.01); *A61B 2017/0404* (2013.01); *A61B 2017/0409* (2013.01); *A61B 2017/0412* (2013.01); *A61B 2017/0414* (2013.01); *A61B 2017/0437* (2013.01); *A61B 2017/0496* (2013.01); *A61B 2017/06052* (2013.01); *A61B 2090/034* (2016.02); *A61B 2090/035* (2016.02)

(58) Field of Classification Search
None
See application file for complete search history.

(56) References Cited

U.S. PATENT DOCUMENTS

| | | | | |
|---|---|---|---|---|
| 2010/0081866 A1* | 4/2010 | Goddard | ............... | A61F 2/0045 600/37 |
| 2011/0077457 A1* | 3/2011 | Deitch | .................. | A61F 2/0045 600/37 |
| 2011/0144417 A1* | 6/2011 | Jagger | .................. | A61F 2/0045 600/30 |

* cited by examiner

*Primary Examiner* — Christine H Matthews
*Assistant Examiner* — Joshua D Lannu
(74) *Attorney, Agent, or Firm* — Coloplast Corp., Coloplast A/S; Nick Baumann

(57) ABSTRACT

A tool includes a brace and a hook. The brace includes two posts extending from a base portion. The two posts include a first post that is spaced a distance apart from a second post, with the first post disposed in a first plane and the second post disposed in a second plane that is not the same as the first plane. A side of the base portion opposite from the first post and opposite from the second post includes a recess formed in the base portion. The hook is connected to a handle. The hook has a first section attached to the handle, a second section that is curved to have a J-hook curvature configured for accessing an obturator foramen of the patient, and a third section including a tip. The tip of the hook is removably insertable into the recess formed in the base portion.

11 Claims, 22 Drawing Sheets

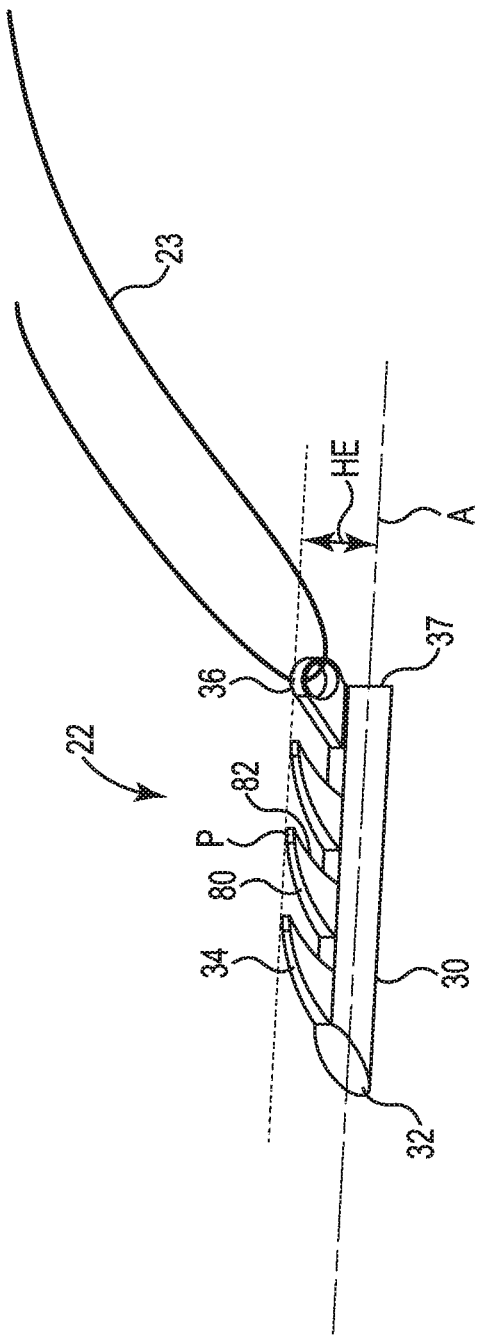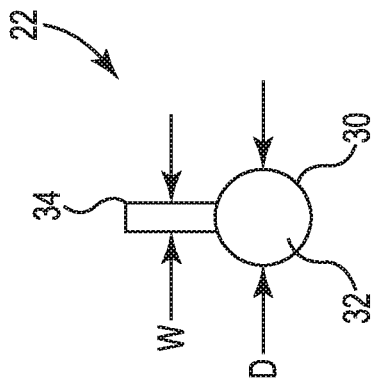
Fig. 2A
Fig. 2B

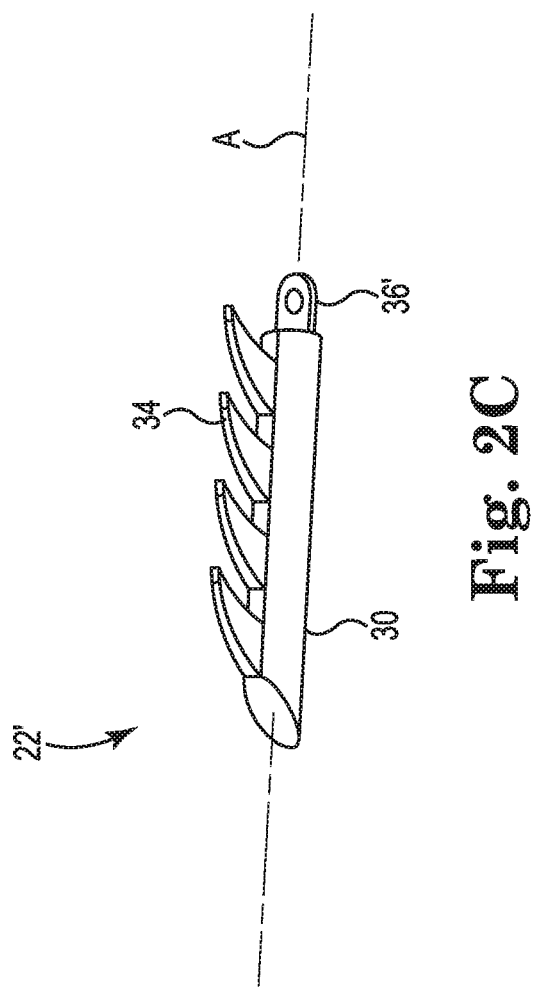

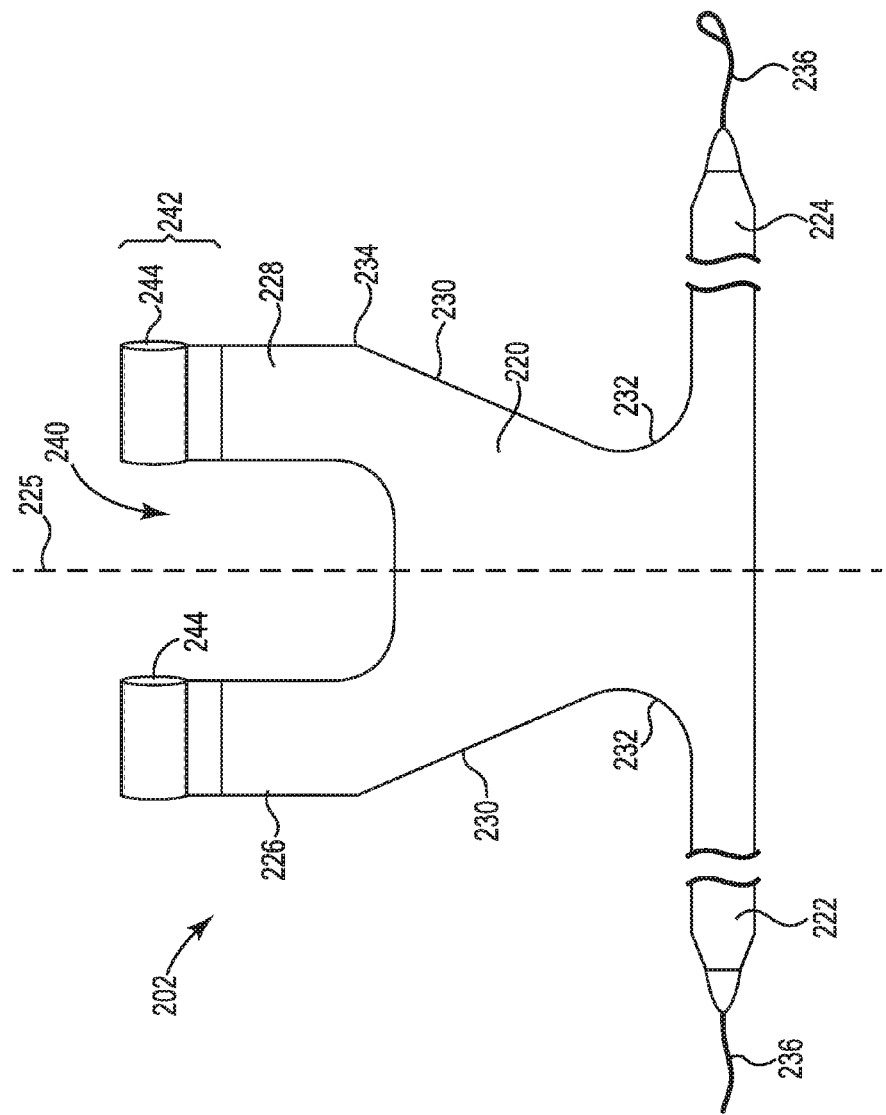

TOOL USEFUL FOR IMPLANTING A SUPPORT IN TREATING URINARY INCONTINENCE IN A PATIENT

BACKGROUND

Intracorporeal suturing of tissue during surgery presents challenges to the surgeon in that the surgeon is called upon to manipulate suturing instruments within the confines of a relatively small incision formed in the patient's body. In some cases, the surgeon is unable to see the suture site. In such a case, the surgeon will digitally palpate with a finger to locate a landmark within the intracorporeal site, and then deliver the suture near at or near the landmark. Tying of the suture inside the patient at the intracorporeal site can be challenging since the surgeon is unable to see the site.

Improved suturing instruments and improved methods of delivering sutures would be welcomed by the surgical staff.

SUMMARY

One aspect provides an incontinence treatment system for a male patient. The system includes a support, a brace attachable to the support, and an introducer provided to deliver an anchor through the support and into periosteum tissue over a pubic bone of the pelvis of the male patient. The support has a body, a pair of lateral arms extending laterally from the body and a pair of longitudinal arms extending longitudinally from the body substantially orthogonal to the lateral arms. A pocket is formed at an end portion of each of the longitudinal arms. The brace includes a base portion, a first post extending from the base portion and a second post extending from the base portion. A first hanger is attached to an end portion of the first post and a second hanger is attached to an end portion of the second post. A first slot is formed between the end portion of the first post and the first hanger and a second slot is formed between the end portion of the second post and the second hanger. Each of the first and second hangers is sized to be inserted into the pocket that is formed at the end portion of each of the longitudinal arms. The anchor has a body, a spine projecting radially away from the body, an eyelet attached to a trailing end of the body, and a suture attached to the eyelet. The introducer has a cannula with a lumen that is sized to receive the body of the anchor and a slot formed through a wall of the cannula that is sized to receive the spine of the anchor. The spine of the anchor is configured to be fixated under the periosteum tissue and the suture is configured to secure the support in contact with the periosteum tissue.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

FIG. 2A is a perspective view of the anchor illustrated in FIG. 1.

FIG. 2B is an end view of the anchor.

FIG. 2C is a perspective view of one embodiment of an anchor for the surgical system illustrated in FIG. 1.

FIG. 10 is a perspective view of one embodiment of a support of the treatment system illustrated in FIG. 9.

DETAILED DESCRIPTION

Figure 1:
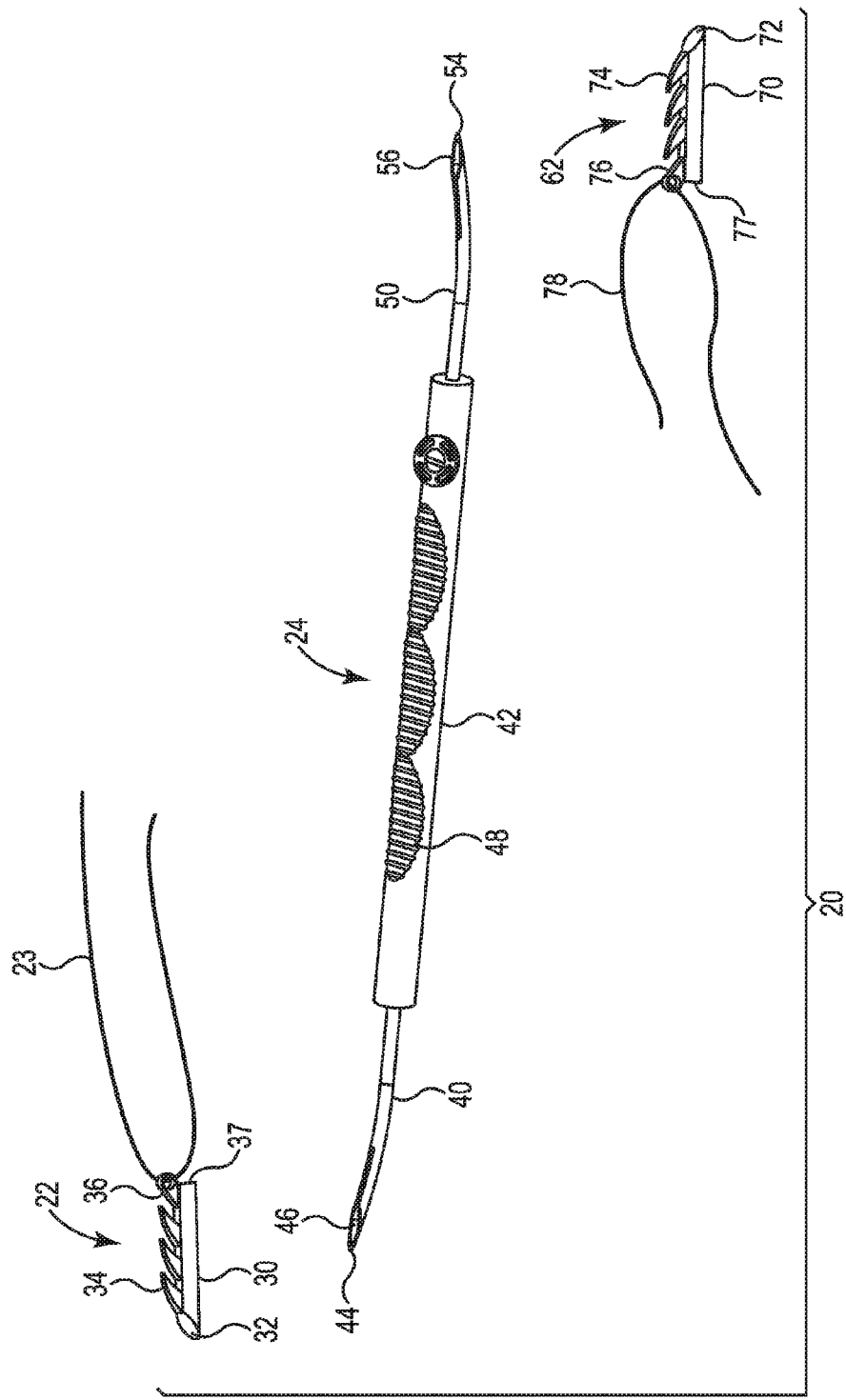
FIG. 1 is a perspective view of one embodiment of a surgical system including an anchor that is insertable into a cannula of an introducer.

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

The features of the various exemplary embodiments described in this application are suitable and intended to be combined with each other, unless specifically noted otherwise.

Anterior means "forward" or "front," and posterior means "rearward" or "back." Relative to surfaces of an organ in the human body, an anterior surface of an instrument inserted into the organ will be oriented forward toward the belly and a posterior surface will be oriented rearward toward the spine.

End means an end most location and end portion means that segment adjacent to and near the end of an object. For example, two opposing ends of an object are each equidistant from a mid-point of the object and between the mid-point and each end of the object is an end portion of the object.

Embodiments provide a surgical system including an introducer that is configured to deliver an anchor to an intracorporeal tissue site. The introducer includes a cannula that allows placement of an anchor at a landmark in tissue deep within an incision site, which may be out of the field of vision of the surgeon. The anchor is configured to be secured within the cannula so that it does not rotate or fall out of the cannula during insertion into the tissue. A length of suture is provided that is attached to the anchor, where the suture may be tied or otherwise terminated to itself outside of the incision site and then subsequently directed to the intracorporeal landmark.

Some incontinence treatment devices have several arms, including some form of arms that traverse the obturator foramen (called transobturator arms) and other arms that are implanted anterior to the pubic bone (called pre-pubic arms). A first set of tools is used to place the transobturator arms and a second, different set of tools is used to place the pre-pubic arms. The pre-pubic arms are tunneled anterior to the pelvis and exit the skin of the abdomen.

In contrast, embodiments of the system described in this specification provide a support with two transobturator arms and a system to attach a portion of the support directly and efficiently to the periosteum tissue. The system obviates the use of additional pre-pubic arms and additional tools that tunnel the pre-pubic arms under the skin. The system is easier to implant compared to a four arm or six arm support, and reduces the amount of time that the patient is in the operating room.

One approach to treating urinary incontinence places a support inferior to the urethra and directs arms upward from the support alongside the bladder along a U-shaped pathway. A significant advance over the U-shaped pathway was provided by Dr. Emmanuel Delorme as described in his U.S. Pat. No. 6,638,211 and included placing arms of a support through the obturator foramen along a V-shaped pathway. This application provides another advance in supporting the pelvic anatomy by recognizing that support material can be robustly attached to the periosteum tissue through the use of an anchoring system. The anchoring system allows the surgeon to place the support inside of the patient and directly fixate the support to periosteum tissue that is present over the exterior of the bones. This approach does away with needles and other tools that tunnel the arms of a support through tissue. The anchoring system described in this application is compatible with a true single (only one) incision formed in the patient.

FIG. 1 is a perspective view of one embodiment of a surgical system 20. The surgical system 20 (system 20) includes an anchor 22 attached to a length of suture 23 and an introducer 24 adapted to deliver the anchor 22 to an intracorporeal landmark. The anchor 22 is sized to be inserted into the introducer 24, and the introducer 24 is sized to be inserted through a single incision to push or direct the anchor 22 into tissue. The suture 23 trails behind the anchor 22 and is available for subsequent ligation of the tissue, or for subsequent attachment of a support to the tissue.

The anchor 22 includes a body 30 having a pointed leading end 32 that is configured to pierce tissue, a spine 34 projecting radially away from the body 30 and configured to engage with or anchor to tissue, and an eyelet 36 attached to a trailing end 37 of the body 30. The length of suture 23 is inserted through the eyelet 36.

The introducer 24 includes a cannula 40 extending from a handle 42. The cannula 40 has a pointed distal end 44 and an opening 46 formed in the cannula 40. The opening 46 or lumen 46 is sized to receive the body 30 of the anchor 22. The handle 42 includes a gripping surface 48 formed on at least one side of the handle 42. It is acceptable to provide the handle 42 with several gripping surfaces or with no gripping surfaces. During a suturing procedure, the anchor 22 is loaded into the opening 46 of the cannula 40 and the surgeon grips the handle 42 and directs the pointed distal end 44 of the cannula to a targeted tissue landmark. Force delivered to the handle 42 in a distal direction will drive the pointed distal end 44 of the cannula 40 into the tissue, such that a subsequent withdrawal of the introducer 24 in a proximal direction will allow the introducer 24 to exit the tissue. The spine 34 (and in some cases the eyelet 36) engages with the tissue, thus leaving the anchor 22 engaged with and deposited in the tissue after the cannula 40 is withdrawn.

In one embodiment, the introducer 24 includes a pair of cannulas, including a second cannula 50 having a pointed distal end 54 and an opening 56 formed in the cannula 50. The second cannula 50 is provided to receive a second, separate anchor. With this in mind, a second anchor 62 is provided having a body 70 having a pointed leading end 72, a spine 74 projecting radially from the body 70, an eyelet 76 attached to a trailing end 77 of the body 70, and a second length of suture 78 attached to the eyelet 76. In this embodiment, the introducer 24 is operable to deliver the first anchor 22 out of the first cannula 40 and to subsequently deliver the second anchor 62 out of the second cannula 50. The gripping surface 48 is configured to allow the translation or rotation of the instrument to selectively move each of the cannulas 40, 50 to a forward facing proximal position.

FIG. 2A is a perspective view of the anchor 22 and FIG. 2B is an end view of the anchor 22. The anchor 22 includes multiple spines 34 extending from the body 30. In one embodiment, the spines 34 project radially away from a center longitudinal axis A of the body 30, with each spine 34 shaped as a shark fin having a curved leading edge 80 that meets with a curved trailing edge 82 at a point P. The curved leading edge 80 is oriented to diverge away from the pointed leading end 32 of the body 30 to allow the anchor 22 to glide into tissue and prevent the anchor from pulling out of the tissue. Although three spines 34 and one eyelet 36 are illustrated, the anchor 22 is also suitably provided with a single spine 34 and one eyelet 36. The anchor 22 is also suitably provided with more than three spines 34.

The eyelet 36 projects radially away from the center longitudinal axis A of the body 30 and as such is also configured to engage with tissue. For example, the eyelet 36 is provided with a height HE that is substantially equal to the height of the spines 34 (the distance that the point P is away from the center axis A). The eyelet has a width substantially equal to the width W of the spine 34.

The body 30 of the anchor 22 is substantially circular in lateral cross-section (FIG. 2B). The anchor 22 is configured to slide in an entry direction through the tissue, and is shaped to prevent withdrawal of the anchor 22 in the direction that is opposite of the entry direction. The curved leading edge 80 of the shark fin shape of the spines 34 facilitate the easy sliding of the anchor 22 through the tissue in the entry direction, and the curved trailing edge 82 of the spines 34 configure the anchor to resist being pulled out of the tissue in the direction that is opposite of the entry direction. In one embodiment, the body 30 of the anchor 22 has a diameter D, and the spine 34 has a width W that is less than about 25% of the diameter D (FIG. 2B).

FIG. 2C is a perspective view of one embodiment of an anchor 22' provided with an eyelet 36' that is disposed on the center longitudinal axis A of the body 30. The spines 34 of the anchor 22' are provided to engage with tissue, and the eyelet 36' is streamlined to follow the body 30 into the tissue channel that is formed when the anchor 22' is driven into the tissue by the introducer 24 (FIG. 1).

Figure 3:
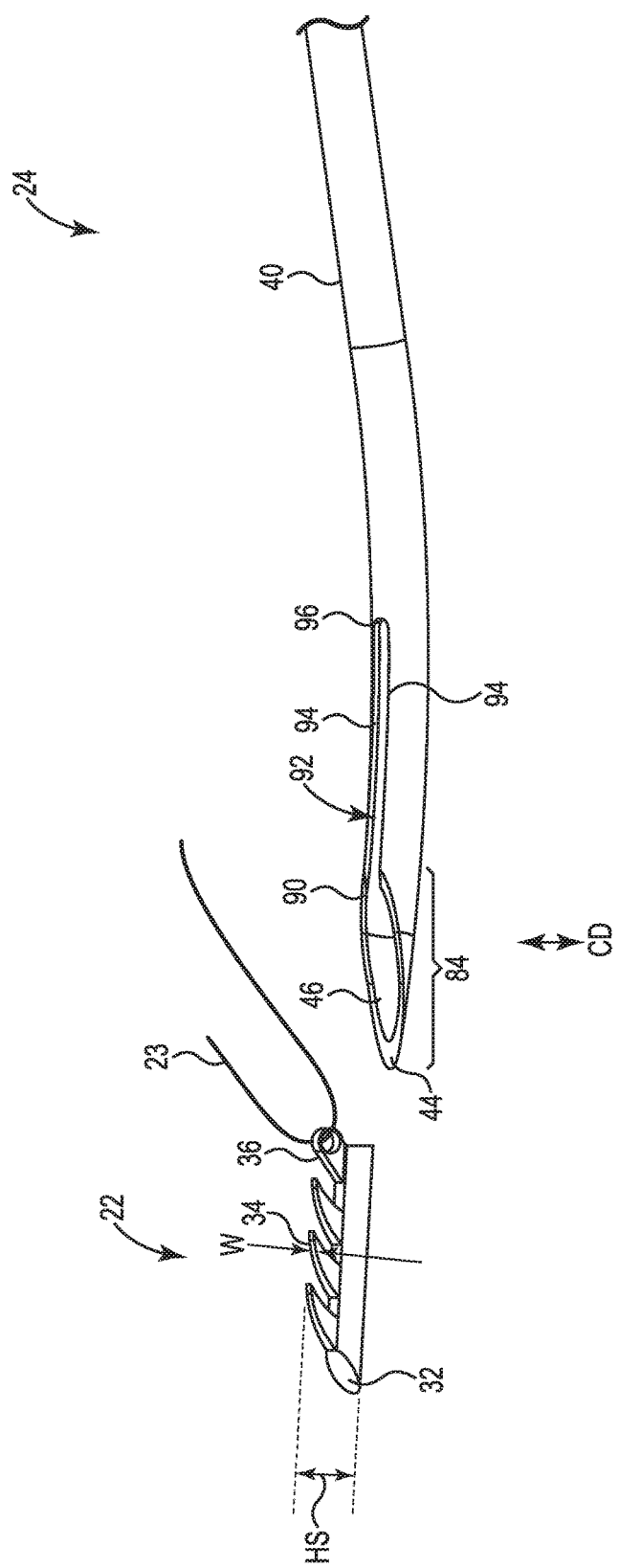
FIG. 3 is a perspective view of the anchor outside of the cannula illustrated in FIG. 1.
Figure 4:
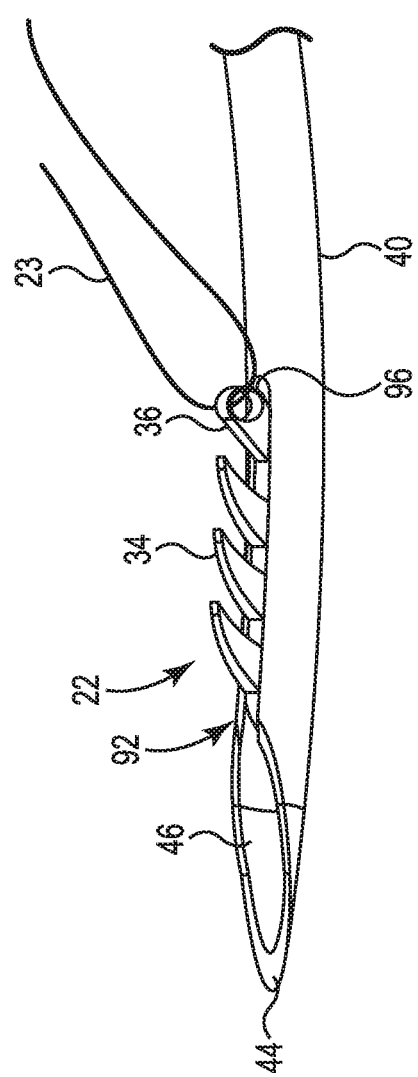
FIG. 4 is a perspective view of the anchor inserted into a lumen of the cannula illustrated in FIG. 1.

FIG. 3 is a perspective view of the anchor 22 positioned for insertion into the cannula 40 of the introducer 24 and FIG. 4 is a perspective view of the anchor 22 inserted into the cannula 40. The body 30 of the anchor 22 is sized to slide into the opening 46 (also called a lumen 46) of the cannula 40 with the spine 34 projecting out of the cannula 40. With reference to FIG. 3, the inside diameter of the lumen 46 of the cannula 40 provides a cannula diameter CD, and the spine 34 has a height HS that is greater than the cannula diameter CD. The height HS the spine 34 is at least 5% greater than the cannula diameter CD. For example, the height HS of the spine 34 is in the range of 5-100% greater than the cannula diameter CD.

It is acceptable for the height HE (FIG. 2A) of the eyelet 36 to be equal to the height HS of the spine 34. It is also acceptable for the height HE (FIG. 2A) of the eyelet 36 to be different from and not equal to the height HS of the spine 34.

The cannula 40 includes a tapered distal end portion 84 that tapers to the pointed distal end 44, where the tapered distal end portion 84 provides the cannula 40 with a needle-like point adapted for insertion through tissue. In some applications, the pointed distal end 44 of the cannula 40 is sharp and needle-like and is so configured to enter the periosteum tissue covering a boney surface and glide under the periosteum tissue and over the bone. In this manner, the cannula is configured to deliver the anchor 22 between the periosteum tissue and the bone.

The cannula 40 has a wall 90 that forms or defines the lumen 46 and a slot 92 formed through the wall 90. The slot 92 is proximal of the tapered distal end portion 84 and extends through the wall 90 to communicate with the lumen 46. The slot 92 includes a pair of opposed longitudinal side edges 94 that extend from a proximal lateral edge 96 in a distal direction to the distal end portion 84. The width of the slot between the longitudinal side edges 94 is sized to receive the width W of the spines 34. The cannula diameter CD is sized to receive the diameter D (FIG. 2B) of the body 30 of the anchor 22.

With reference to FIG. 4, when the anchor 22 is loaded into the cannula 40, the pointed leading end 32 of the body 30 is located proximal of the pointed distal end 44 of the cannula 40, and the spines 34 and the eyelet 36 extend outside of the cannula 40 and are positioned to engage with tissue during implantation of the anchor 22. The proximal lateral edge 96 of the slot 92 is positioned to push against the eyelet 36 and drive the anchor 22 into the tissue. The opposed longitudinal side edges 94 of the slot 92 provide a stanchion that restrains the spines 34 and prevents the anchor 22 from rotating relative to the cannula 40. The spines 34 and the eyelet 36 slide in a longitudinal direction relative to the slot 92 to allow the cannula 40 to be removed from the tissue while leaving the anchor 22 implanted.

Suitable materials for fabricating the anchor 22 include plastics, or metal, or sintered material. One suitable material for fabricating the anchor 22 is polypropylene. Another suitable material for fabricating the anchor 22 is a bioabsorbable polymer that configures the anchor 22 to be absorbed into the body over a period of several weeks.

Suitable materials for fabricating the length of suture 23 include bio-inert components that do not bioabsorb, or bioabsorbable components that are configured to be absorbed or resorbed by the body. One suitable material for fabricating the length of suture 23 is polypropylene. Other suitable materials for fabricating the length of suture 23 include dissolvable sutures available from Ethicon™, a J&J Company located in Somerville, N.J., and include Monocryl™ (polyglycaprone 25) sutures, coated Vicryl™ (polyglactin 910) sutures, Ethicon Plus™ Sutures, or polydioxanone sutures as examples.

Suitable materials for fabricating the cannula 40 and include plastics or metal. One suitable material for fabricating the cannula 40 is stainless steel. Other suitable materials are acceptable.

With reference to FIG. 1, the anchor 22 is useful for fixating a support material within a patient's body. The introducer 24 is sized to place the anchors 22 through a single incision and into the periosteum tissue that covers the pubic bone, examples of which are described below.

Figure 5:
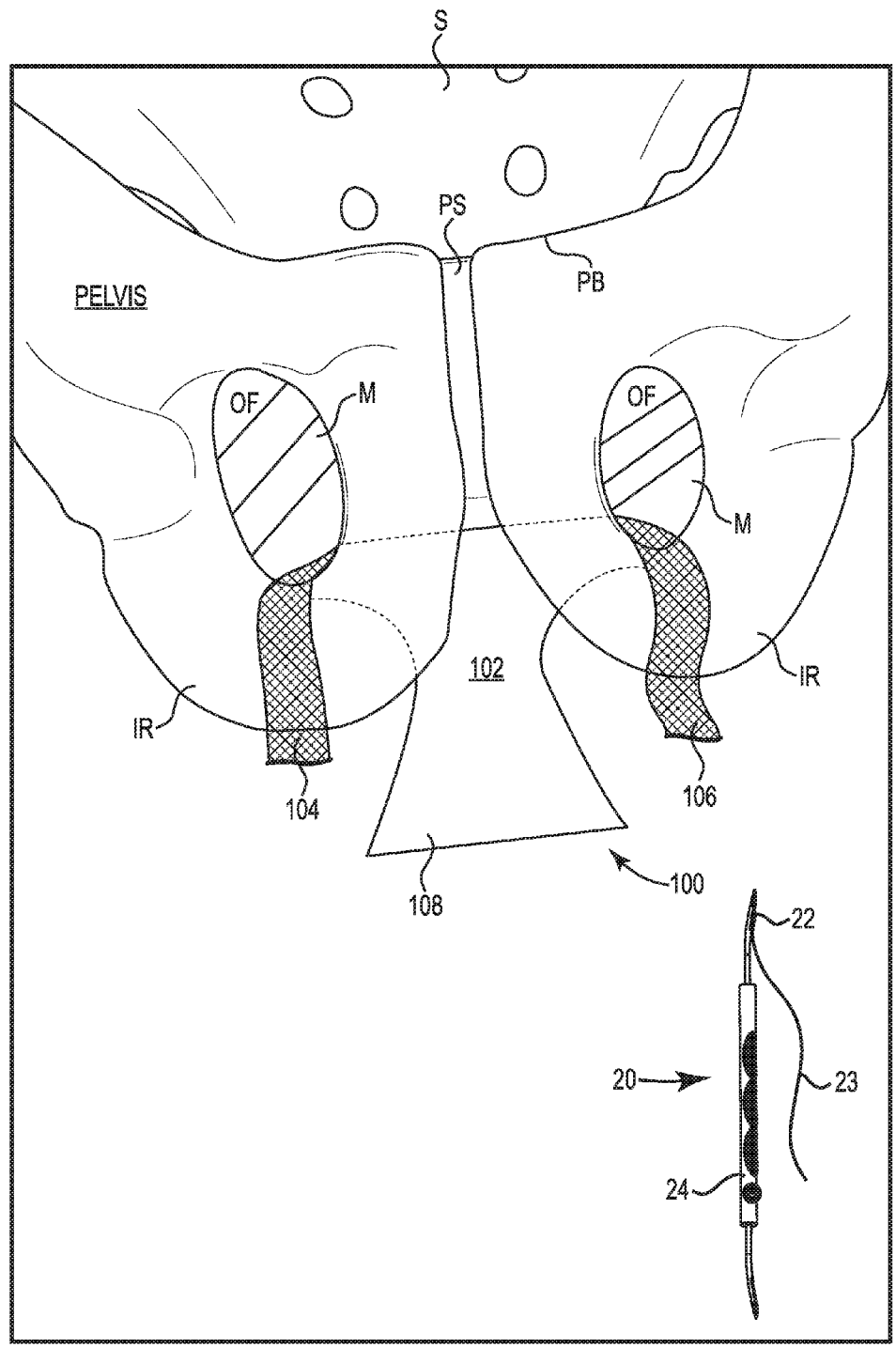
FIG. 5 is a schematic view of one embodiment of the surgical system provided to anchor a support material to tissue of the human body, with the support material having an arm inserted through each of two obturator foramen of the pelvis.

FIG. 5 is a schematic view of one embodiment of a support 100 attachable to a pelvis of a patient. FIG. 5 provides an anterior view of the pelvis with the sacrum S located in a posterior portion of the view, with the pubic symphysis PS centered relative to the pubic bone PB, and an obturator foramen OF on each bilateral side of the pelvis. Each obturator foramen OF provides an opening or a window that is covered by a membrane M. Nerves and arteries traverse the upper reaches of the obturator foramen OF. The membrane M generally includes several layers of muscle and at least one layer of ligament-like tissue that connects the muscles in the membrane M to the pelvis. The ischial pubic ramus IR is located inferior to the pubic bone PB and the obturator foramen OF.

The support 100 is provided to elevate and compress the male urethra and includes a body 102, a first arm 104 extending from the body 102, a second arm 106 extending from the body 102, and a pre-pubic portion 108 that is oriented in a generally orthogonal position relative to the arms 104, 106. The illustrated embodiment is a two-arm device.

Suitable materials for fabricating the support 100 include porous materials that allow tissue ingrowth throughout the support structure to anchor the support 100 in the body after implantation and healing. Suitable such porous materials include autograft material (the patient's own tissue), allograft material (tissue from a cadaver), xenograft material (tissue from another species), or synthetic materials such as woven fabrics, meshes, nonwoven fabrics, meshes, fibrillated fibers, or spun and fibrillated fibers that are provided with voids (pores) configured to allow tissue ingrowth into the support 100. The pores are generally larger, on average, than 75 μm.

The support 100 is attached to the pelvis with each arm 104, 106 inserted into one of the respective obturator foramen OF, and with the pre-pubic portion 108 attached to the periosteum tissue that lines the exterior of the pubic bone PB. The following surgical procedure is one example of the suitable implantation of the support 100 into a male patient.

The patient is positioned on a surgical operating table in a lithotomy, or modified lithotomy position, and is anesthetized. A vertical midline perineal incision 110 (see FIG. 6) is formed between the scrotum and the anus. Tissue is dissected to expose the bulbous muscle around the urethra. A suitable tool is used to direct the arm 104 into and through the first obturator foramen OF, and this procedure is repeated on the contralateral side to place the arm 106 into and through the second obturator foramen OF.

One suitable approach of placing the arms 104, 106 through the obturator foramen OF is described as an "outside-in" approach. The outside-in approach includes directing a needle or other device through the skin of the groin area of the patient external of the obturator foramen OF along a curved path through the membrane M and around the ischial pubic ramus R such that the tool exits the midline perineal incision 110. One of the arms 104, 106 is attached to the tool, and the tool is withdrawn along its curved pathway back around the ischial pubic ramus IR, through the membrane M, out of the obturator foramen OF, and out of the skin at the groin area. In this manner, each arm 104, 106 is directed through and placed in one of the obturator foramen OF. The arms 104, 106 are trimmed to a subcutaneous level. A holding stitch is placed to hold the arm 104, 106 relative to the groin tissue, as determined by the surgeon.

A different approach is the "inside-out" approach in which the needle or tool is coupled to the support and directed from the perineal incision (inside) outward to the skin at the groin area (outside). Placement of the arms 104, 106 with the inside-out approach is also acceptable.

One acceptable single incision approach includes the formation of a single (exactly one) incision in the urogenital triangle. Tissue is dissected distal the incision to access the urethra and the pelvis. The arms 104, 106 of the support 100 are directed into the single incision and anchored to the membrane M of the obturator foramen OF, for example with the anchor 22 (FIG. 1). The pre-pubic portion 108 is inserted into the single incision and fixed to the periosteum tissue over the pubic bone PB by the anchor 22 as delivered by the introducer 24. In this manner, a treatment for urinary incontinence is provided to the patient by forming exactly and only one incision and implanting the support 100 through that single incision.

Figure 6:
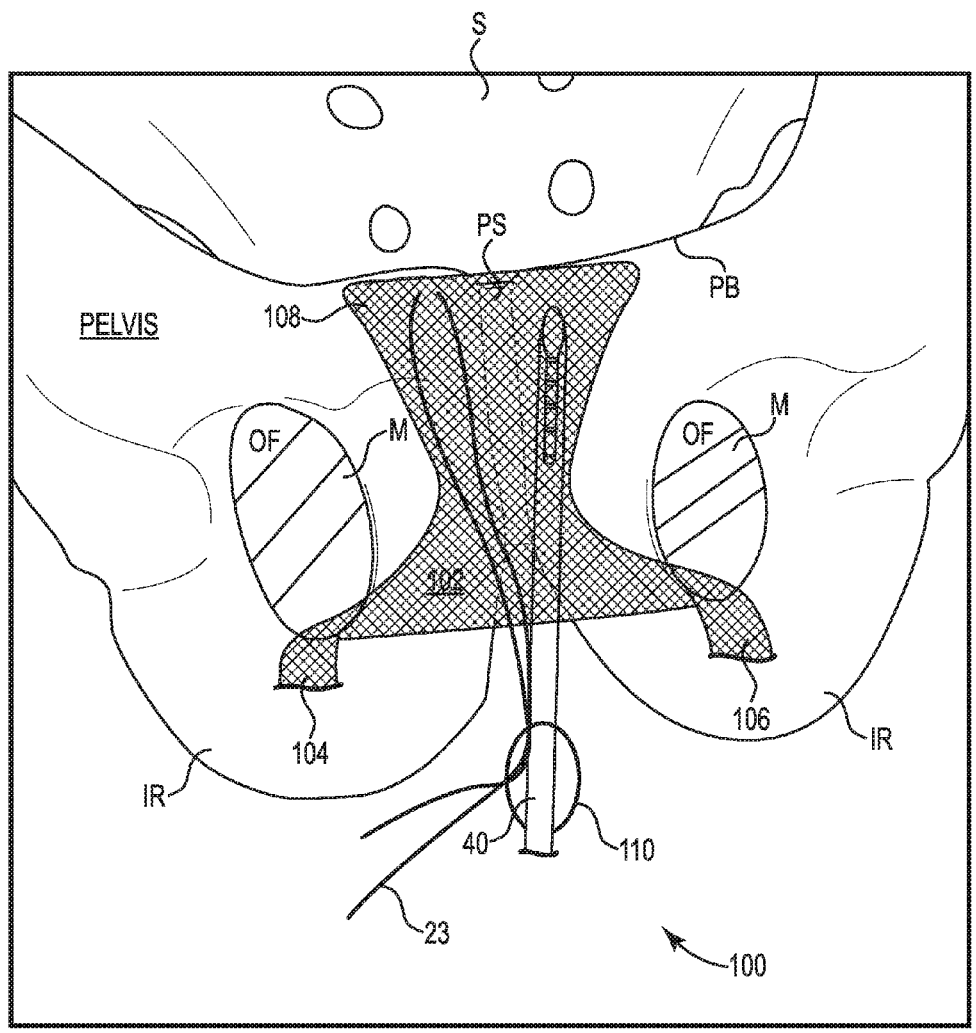
FIG. 6 is a schematic view of one embodiment of the surgical system employed to anchor a support material to the tissue of the human body showing a pre-pubic portion being attached to the periosteum of the pubic bone.

FIG. 6 is a schematic view of the surgical system 20 employed to fixate the pre-pubic portion 108 of the support 100 to the periosteum tissue of the pubic bone PB. The cannula 40 of the introducer 24 is inserted into the perineal incision 110 and directed to the pubic bone PB anterior to the pelvis.

In one suitable approach, the anchor 22 is driven through the material of the support 100 and into the periosteum tissue that covers the pubic bone PB. The cannula 40 pierces the periosteum tissue and slides along the bone of the pelvis without entering or penetrating the bone. The anchor 22 is engaged under the periosteum tissue and the suture 23 extends through the support 100 out through the perineal incision 110. The surgeon, depending upon surgeon preference, will place at least one anchor 22 through the pre-pubic portion 108 an each side of the pubic symphysis PS. The suture 23 extends from each anchor out through the perineal incision 110 and is available for subsequent tying or other termination.

In a different suitable approach, the anchor 22 is loaded into the introducer 24 and the cannula 40 is introduced in the perineal incision 110 up to the pubic bone PB anterior to the pelvis. The introducer 24 is employed to drive the anchor 22 under the periosteum tissue of the pubic bone PB and the cannula 40 is withdrawn through the perineal incision 110. The suture 23 trails behind the anchor 22 and exits the body at the incision 110. An end of the suture 23 is inserted through the pre-pubic portion 108 of the support 100, and the pre-pubic portion 108 is guided along the suture 23, through the incision 110, and up to the pubic bone PB. Thereafter, the suture 23 is tied or terminated to hold the pre-pubic portion 108 against the pubic bone.

Figure 7:
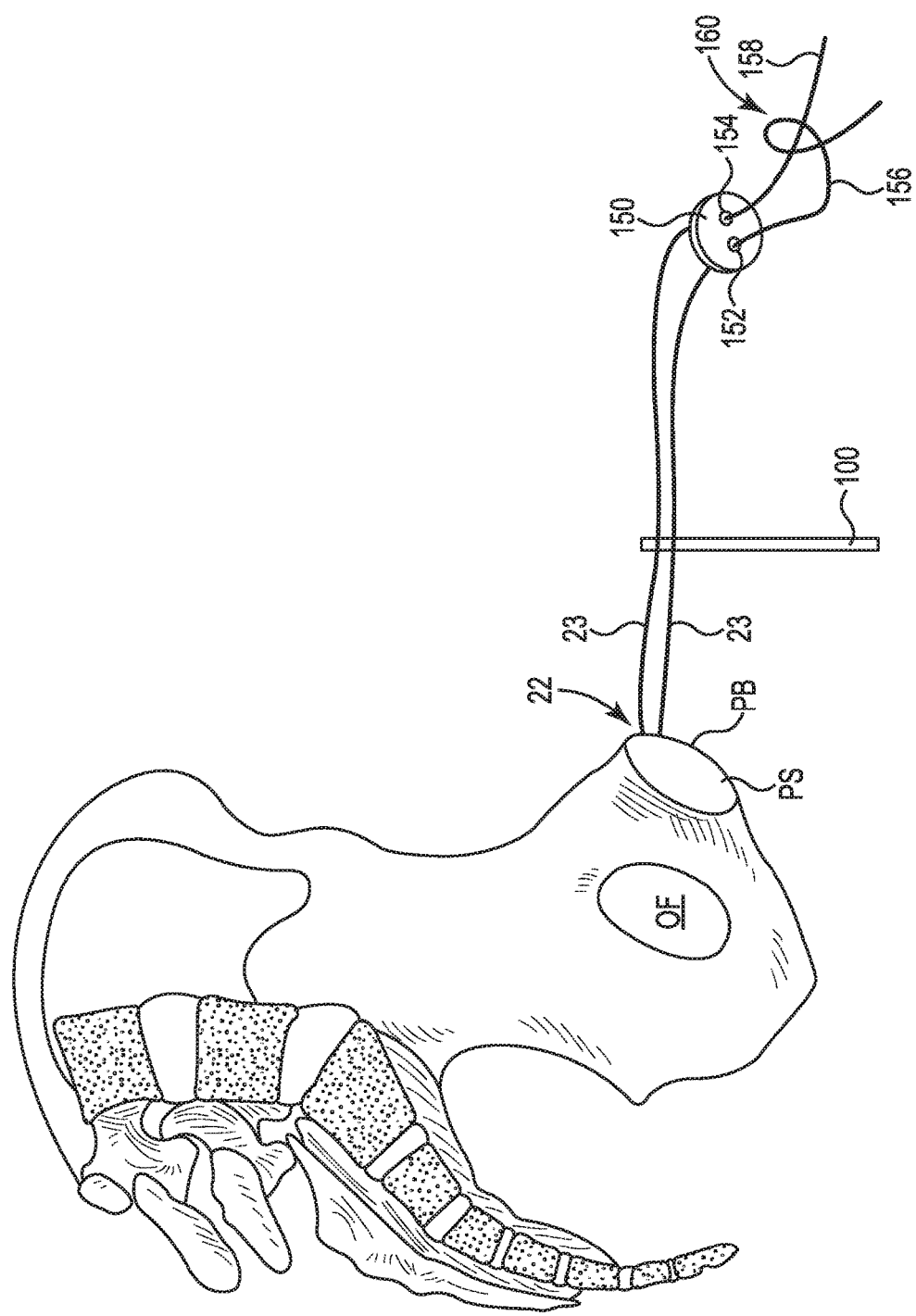
FIG. 7 is a schematic view of the anchor illustrated in FIG. 1 secured to tissue with a stopper coupled with a suture and located between the anchor and a slip knot.

FIG. 7 is a schematic view of the anchor 22 secured to the periosteum tissue and the support 100 secured to the suture 23. In one embodiment, the system 20 described above includes a stopper 150 that is attached to the suture 23, where the stopper 150 is configured to slide along the suture 23 and direct the support 100 into the patient's body and against the tissue. In one embodiment, the stopper 150 has a first orifice 152 and a second orifice 154. One or more of the anchors 22 is engaged with the periosteum tissue of the pubic bone PB, and a first end 156 of the suture 23 extends from the anchor 22 through the first orifice 152, and a second end 158 of the suture 23 extends to the second orifice 154. The stopper 150 slides along the suture 23 and is operable to push or otherwise deliver the support 100 against the pubic bone PB. In one embodiment, a slip knot 160 or other termination device is provided to tie the suture 23 against the stopper 150 after the stopper 150 and the support 100 has been delivered to the pubic bone PB. The stopper 150 is located between the anchor 22 and the slip knot 160.

Suitable materials for fabricating the stopper 150 include plastics or metal. One suitable material for fabricating the stopper 150 includes polypropylene. Another suitable material for fabricating the stopper 150 includes stainless steel. In one embodiment, the stopper 150 is fabricated to be bioabsorbable.

Figure 8:
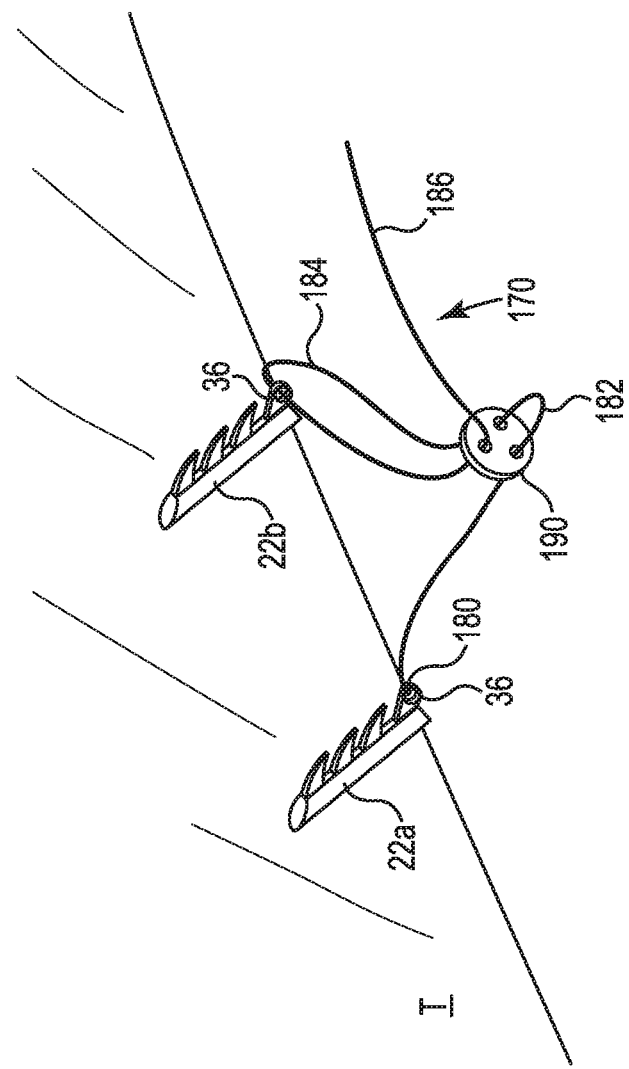
FIG. 8 is a schematic view of two anchors as illustrated in FIG. 1 secured to tissue and coupled with a suture.

FIG. 8 is a schematic view of two anchors 22 secured to tissue T and coupled with a suture 170. The anchors include a first anchor 22a and a second anchor 22b. The anchors 22 are engaged with the tissue T, for example through the use of the introducer 24 (FIG. 1). A suture 170 is provided having a first end 180 terminated to the eyelet 36 of the anchor 22a, a mid-portion 182 of the suture located between the first anchor 22a and the second anchor 22b, and a portion 184 of the suture in sliding engagement with the eyelet 36 of the second anchor 22b. A free end 186 of the suture 170 is provided, and pulling on the free end 186 of the suture 170 cinches the mid-portion 182 of the suture between the first anchor 22a and the second anchor 22b. In one embodiment, a slide knot 190 or sliding engagement feature 190 or slip knot 190 is coupled to the suture 170 and is so configured to secure or lock the mid-portion 182 of the suture in a desired position relative to the anchors 22. The slide knot 190 operates to cinch the suture 170 tightly against the support 100 (FIG. 6) against the tissue T.

Some male incontinence treatment devices have several arms, including some form of arms that traverse the obturator foramen and other arms that are implanted anterior to the pubic bone (called pre-pubic arms). The pre-pubic arms are tunneled anterior to the pelvis and exit the skin of the abdomen.

In contrast, embodiments of the system described above provide a support with two arms that are A) secured to the periosteum alongside the obturator foramen or B) secured to the membrane M covering the obturator foramen or C) secured through the obturator foramen and a system 20 to attach a portion of the support directly and efficiently to the periosteum tissue over the pubic bone. The system obviates the use of additional pre-pubic arms that are tunneled under and affixed to the skin. The system is easier to implant and reduces the amount of time that the patient is in the operating room.

Figure 9:
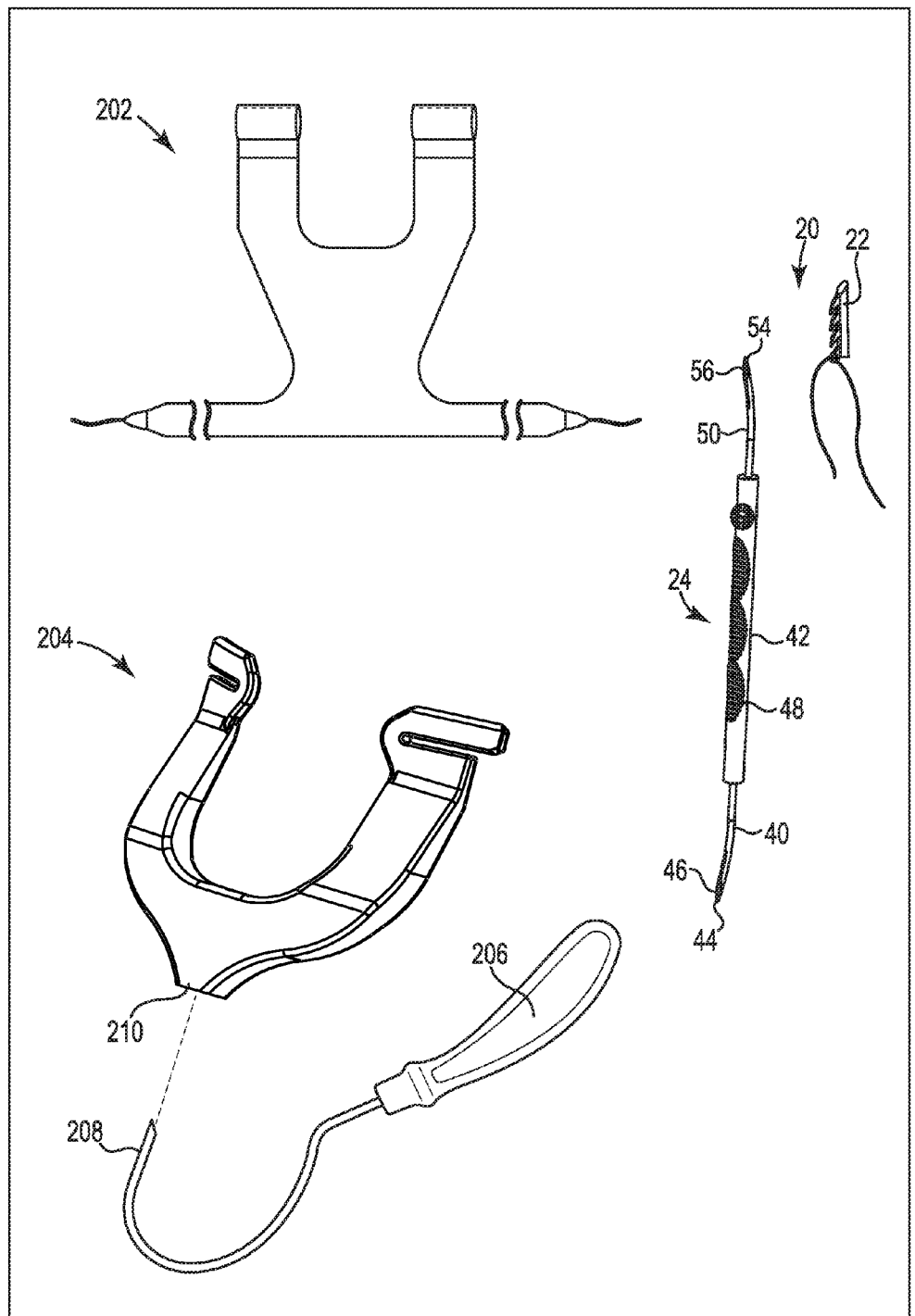
FIG. 9 is a schematic view of one embodiment of a male incontinence treatment system.

FIG. 9 is a schematic view of one embodiment of a male incontinence treatment system 200 (system 200). The system 200 includes a support 202 and a brace 204 that is operable to hold the support 202 in position while the surgeon uses the suture system 20 to place the anchor 22 through the support 202 and into the periosteum tissue. The suture system 20 provides the means for anchoring each of the pair of arms of the support to periosteum tissue of the pelvis.

The support 202, as described in FIG. 10, generally includes a pair of lateral arms that are sized and operable for insertion through one of the obturator foramen on each bilateral side of the pelvis, and an upper pre-pubic portion that is attachable to periosteum tissue on either side of the pubic symphysis.

The brace 204 is generally U-shaped and is sized or configured to hold the upper (or top) pre-pubic portion of the support 202. In one embodiment, the brace 204 is attachable to a J-hook device 206. The J-hook device 206 is available from Coloplast Corp., Minneapolis, Minn. and has utility in the implantation of the arms of the four-arm male urethra support sold under the brand name Coloplast VIRTUE® male sling. The device 206 has dual utility; the device 206 is useful in implanting lateral arms of the support 202 through obturator foramen of the pelvis; and the hook 208 of the device 206 is insertable into the brace 204 to provide a handle useful in manipulating the brace 204 when implanting the longitudinal arms of the support 202. The J-shaped hook 208 is insertable into a recess or a slot 210 formed in the base of the brace 204.

FIG. 10 is a perspective view of the support 202. The support 202 includes a body 220, a pair of lateral arms 222, 224 extending from the body 220 laterally relative to a central longitudinal axis 225, and a pair of longitudinal arms 226, 228 extending from the body 220 longitudinally and parallel to the longitudinal axis 225.

The body 220 is non-rectangular. In FIG. 10, the body 220 includes a pair of tapering sides 230 that converge to the lateral arms 222, 224. The pair of tapering sides 230 diverges or expands in an upward direction to a top portion 234 from which the longitudinal arms 226, 228 extend. A curved juncture 232 is connected between the tapering sides 230 and the lateral arms 222, 224. Thus, the body 220 is narrower at the juncture 232 than it is at the top portion 234 from which the longitudinal arms 226, 228 extend.

The lateral arms 222, 224 extend a distance away from the body 220 that is selected to allow the arms 222, 224 to be sized for insertion through the obturator foramen on each bilateral side of the human pelvis. In one embodiment, a suture line 236 is attached to an end of each of the lateral arms 222, 224. The suture line 236 includes a loop or some other engagement device that allows the suture line 236 and its respective arm 222, 224 to be pulled through the obturator foramen.

The longitudinal arms 226, 228 extend from the top portion 234 of the body 220 and provide a relief area 240 or an opening 240 between the arms 226, 228 that is sized to provide clearance around the male urethra (specifically, the male bulbar urethra). The opening 240 is U-shaped although other shapes for the opening 240 are within the scope of the claimed subject matter of this application.

Each of the longitudinal arms 226, 228 include an upper end portion 242 that forms a pocket 244. In one embodiment, each pocket 244 extends entirely through the lateral width of the longitudinal arms 226, 228. In one embodiment, each pocket 244 extends only a portion of the way through the lateral width of the longitudinal arms 226, 228. The pockets 244 are sized to receive a hanger that is provided by the brace 204 (FIG. 9).

The support 202 is fabricated from synthetic material such as polypropylene or other suitable polymer(s). In one embodiment, the support 202 is a polypropylene mesh provided with pores sizes or openings that allow tissue to grow through the support 202 after it is implanted in the patient.

Figure 11A:
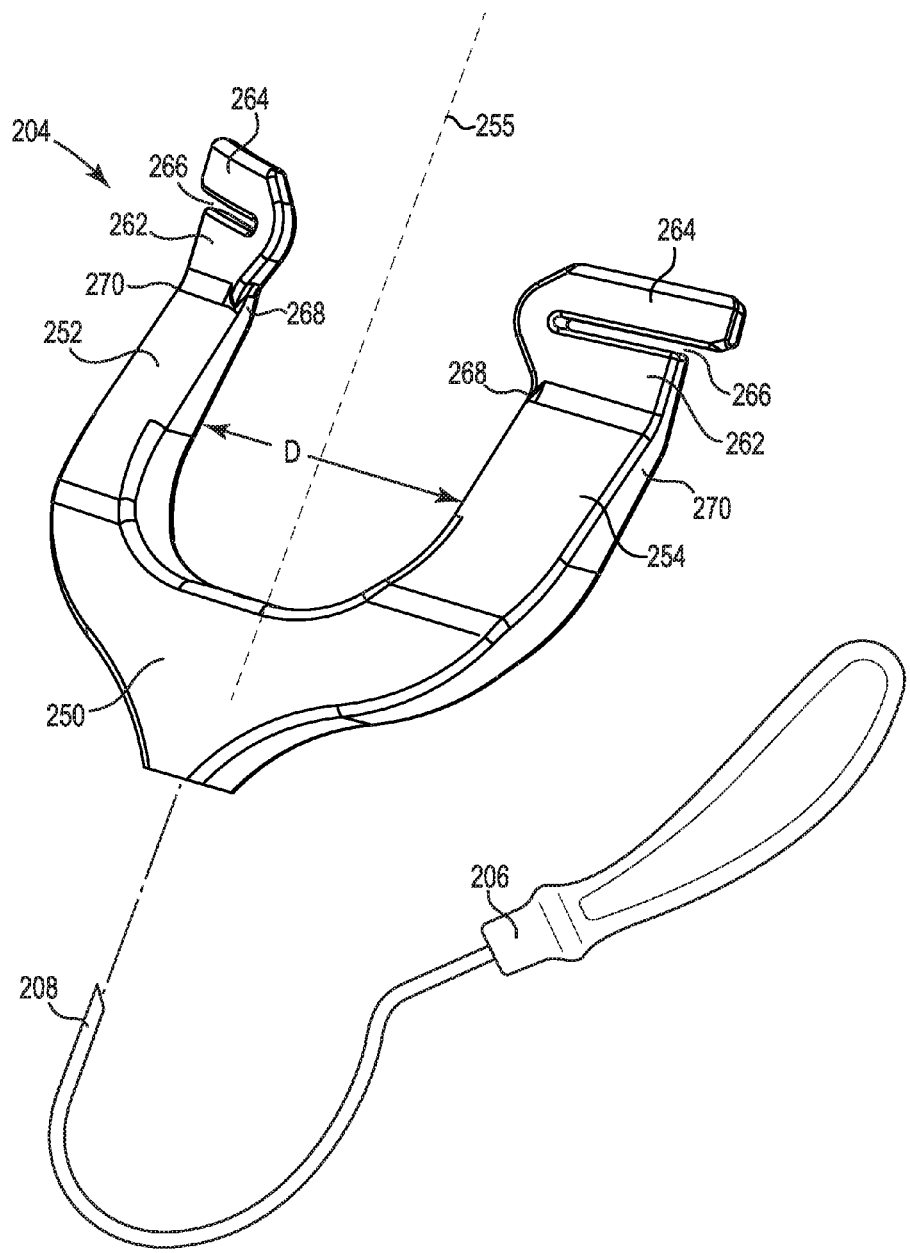
FIG. 11A is a perspective proximal view.
Figure 11B:
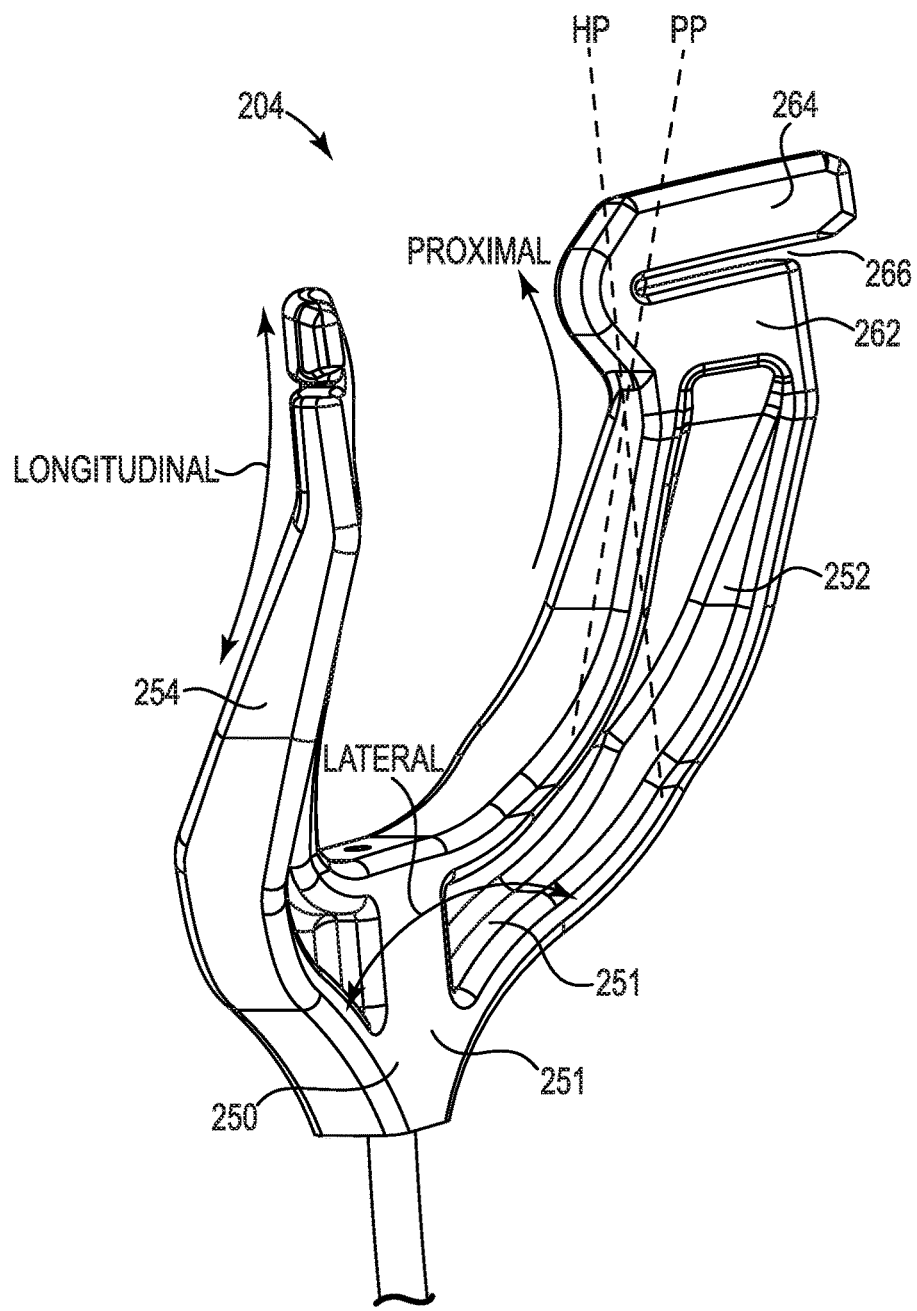
FIG. 11B is a perspective distal view.
Figure 11C:
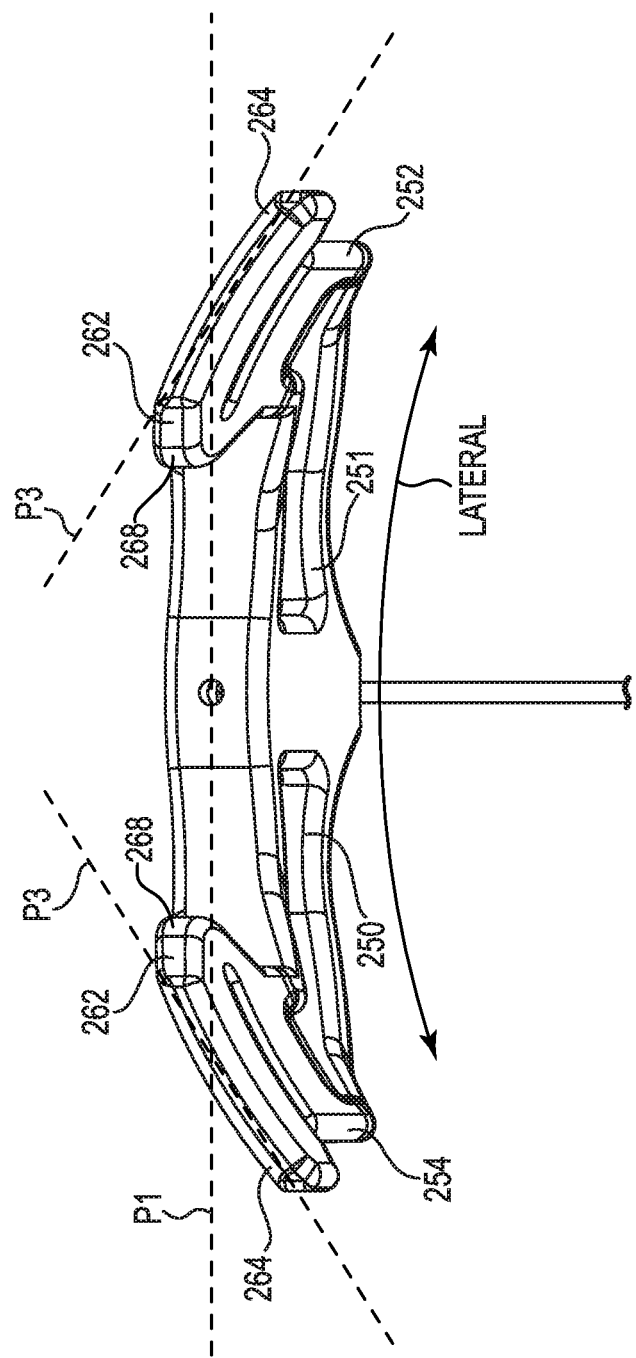
FIG. 11C is a top view of one embodiment of a brace of the treatment system illustrated in FIG. 9.

FIG. 11A is a perspective proximal view (i.e., the rear side of the brace 204 nearest to the surgeon), FIG. 11B is a perspective distal view, and FIG. 11C is a top view of the brace 204. The brace 204 includes a base portion 250 and two posts 252, 254 extending longitudinally and parallel relative to a central longitudinal axis 255 of the base portion 250. Each of the two posts 252, 254 terminate in an end portion 262, and include a hanger 264 is attached to each respective end portion 262. The hanger 264 is formed as a lateral flange (oriented orthogonal to the axis 255) that is spaced apart from the end portion 262 of the posts 252, 254 by a slot 266. In one embodiment, each of the posts 252, 254 has an inside edge 268 and an outside edge 270. Each hanger 264 is attached to and extends away from the inside edge 268 of the posts 252, 254.

The height of the hanger 264 is sized for insertion into the pocket 244 (FIG. 10) of the support 202. The slot 266 allows the hanger 264 to enter into the pocket 244 while each of the posts 252, 254 is located in front of (or anterior to) the longitudinal arms 226, 228 of the support 202. In this manner, the brace 204 is operable to hold the support 202 against the pelvis to allow the introducer 24 (FIG. 1) to access the longitudinal arms 226, 228 of the support 202. The first post 252 is spaced a gap distance D apart from a second post 254, and the gap distance D is sized for placement around a bulbous urethra of the male patient. In addition, the brace 204 includes multiple curvatures that are configured to provide clearance for posts 252, 254 relative to the male bulbar urethra.

FIG. 11B illustrates that the brace 204 has a lateral curvature and a longitudinal curvature. Regarding the lateral curvature, a distal side 251 of the base portion 250 is curved in a cup-like shape that provides the base portion 250 with an arched hump in the proximal direction. The proximal direction is in the direction of the surgeon (away from the patient), and the distal side 251 is oriented toward the patient. The base portion 250 has a lateral curvature such that the distal side 251 is concave and the proximal side (opposite the distal side 251) is convex with an arch formed in the base portion 250 in a proximal direction. The lateral curvature of the base portion 250 thus provides clearance for the brace 204 around the projecting bulbar urethra of the male patient.

Regarding the longitudinal curvature, the first post 252 and the first hanger 264 are curved to arch back in the proximal direction as illustrated by the "proximal" arrow in FIG. 11B such that a portion of the first post 252 is in a post plane PP and the hanger 264 is in a hanger plane HP. The post plane PP is not in the same plane as the hanger plane HP, and as such, the first post 252 is not co-planar (e.g., not in the same plane) with the first hanger 264.

FIG. 11C illustrates a first plane P1 co-planar (in the same plane) with the base portion 250, a second plane P2 co-planar with the first hanger 264 of the first post 252, and a third plane P3 co-planar with the second hanger 264 of the second post 254. The lateral curvature of the base portion 250 provides a concave curvature relative to a distal side 251 of the base portion 250 that is configured to provide clearance around the bulbar urethral complex of the male patient as the brace 204 holds the support 202 in place.

The second plane P2 in the plane of the first hanger 264 is not co-planar with the third plane P3 of the second hanger 264. Each of the posts 252, 254 includes a longitudinal curvature (into the paper in the view of FIG. 11C) such that each respective hanger 264 is not co-planar with its respective post 252, 254. In addition, the hanger 264 of the first post 252 is not co-planar with the hanger 264 of the second post 254.

The longitudinal curvature and the lateral curvature provide the brace 204 with complex curvature in at least two directions. The proximal side of the brace 204 is adapted to be oriented away from the male patient and the distal side 251 is adapted to be oriented toward the male patient. The brace has a complex curvature including a concave lateral curvature formed in the distal side 251 of the base portion 250 of the brace 204 and a concave longitudinal curvature formed in the proximal side of the two posts 252, 254 of the brace 204.

FIGS. 12-19 are schematic views of embodiments of implanting the support 202 using the male incontinence treatment system 200 shown in FIG. 9.

Figure 12:
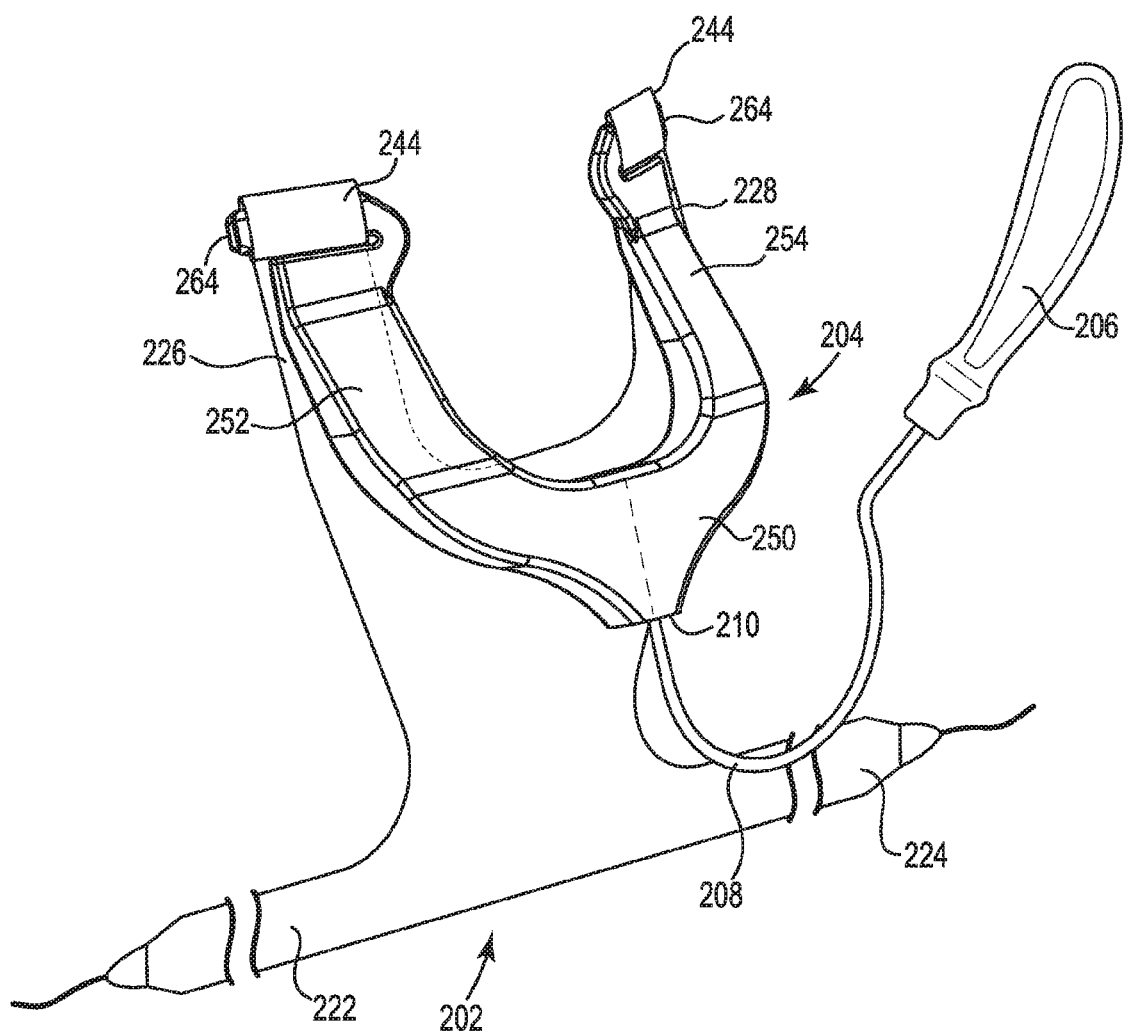
FIGS. 12-19 are schematic views of embodiments of implanting a support using the male incontinence treatment system illustrated in FIG. 9.

FIG. 12 is a perspective view of the brace 204 engaged with the support 202. The hangers 264 of the brace 204 are inserted into the pockets 244 of each of the longitudinal arms 226, 228 of the support 202. The hook 208 of the device 206 is inserted into the recess 210 formed in the base portion 250 to provide the brace 204 with a handle that is useful as a lever when manipulating the brace 204. The U-shape of the brace 204 is adapted to hold the longitudinal arms 226, 228 one on each side of the pubic symphysis of the pelvis to allow the surgeon to attach the longitudinal arms 226, 228, as described below. The lateral arms 222, 224 are typically implanted into the patient before the placement of the longitudinal arms 226, 228.

Figure 13:
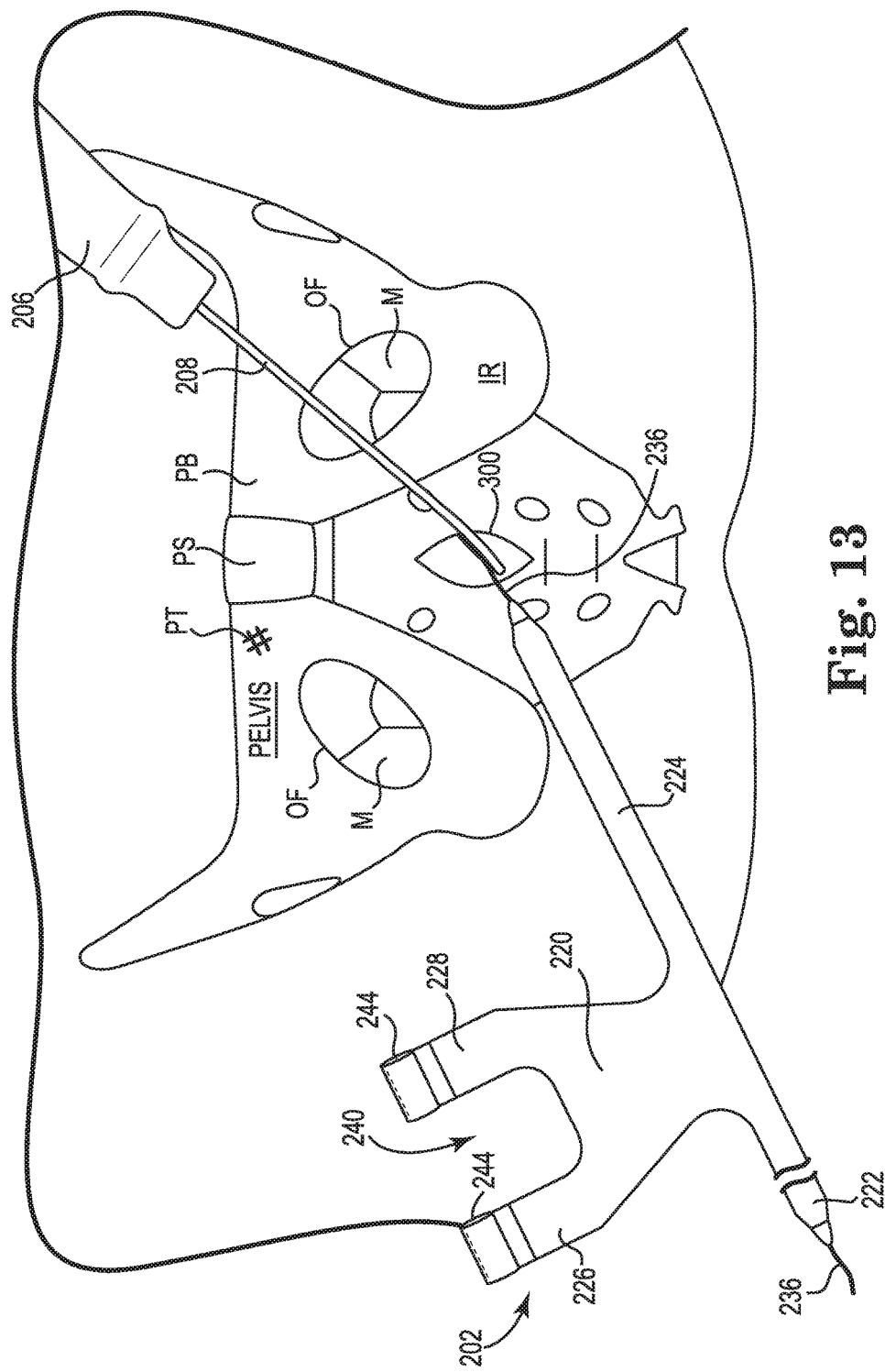

FIG. 13 is a schematic view of a male pelvis. The patient is oriented in a lithotomy position with the knees above the pelvis, which orients the pelvis for access to the perineum. An incision 300 is formed in the perineum (i.e., in the urogenital triangle) of the male patient, and the pelvic tissue is suitably dissected to expose the bulbar urethra and other structural landmarks in the pelvis. The incision 300 is illustrated schematically as an ellipsoid in FIG. 13. A tissue retractor is often used to dilate the incision 300 to a larger and more circular shape to provide an the surgeon with an access window to the pelvic anatomy.

The device 206 is useful in implanting the lateral arms 222, 224 of the support 202. The distal end of the hook 208 is attached to the suture line 236 and inserted into the incision 300. The device 206 is oriented at about a 45° angle relative to the midline of the patient (as illustrated). The J-hook of the device 206 is introduced through the incision 300, posterior to the ischial pubic ramus IR, and the distal end of the hook 208 and the suture line 236 are pushed through the membrane M of the obturator foramen OF, which directs the arm 224 of the support 202 through the obturator foramen OF.

Figure 14:
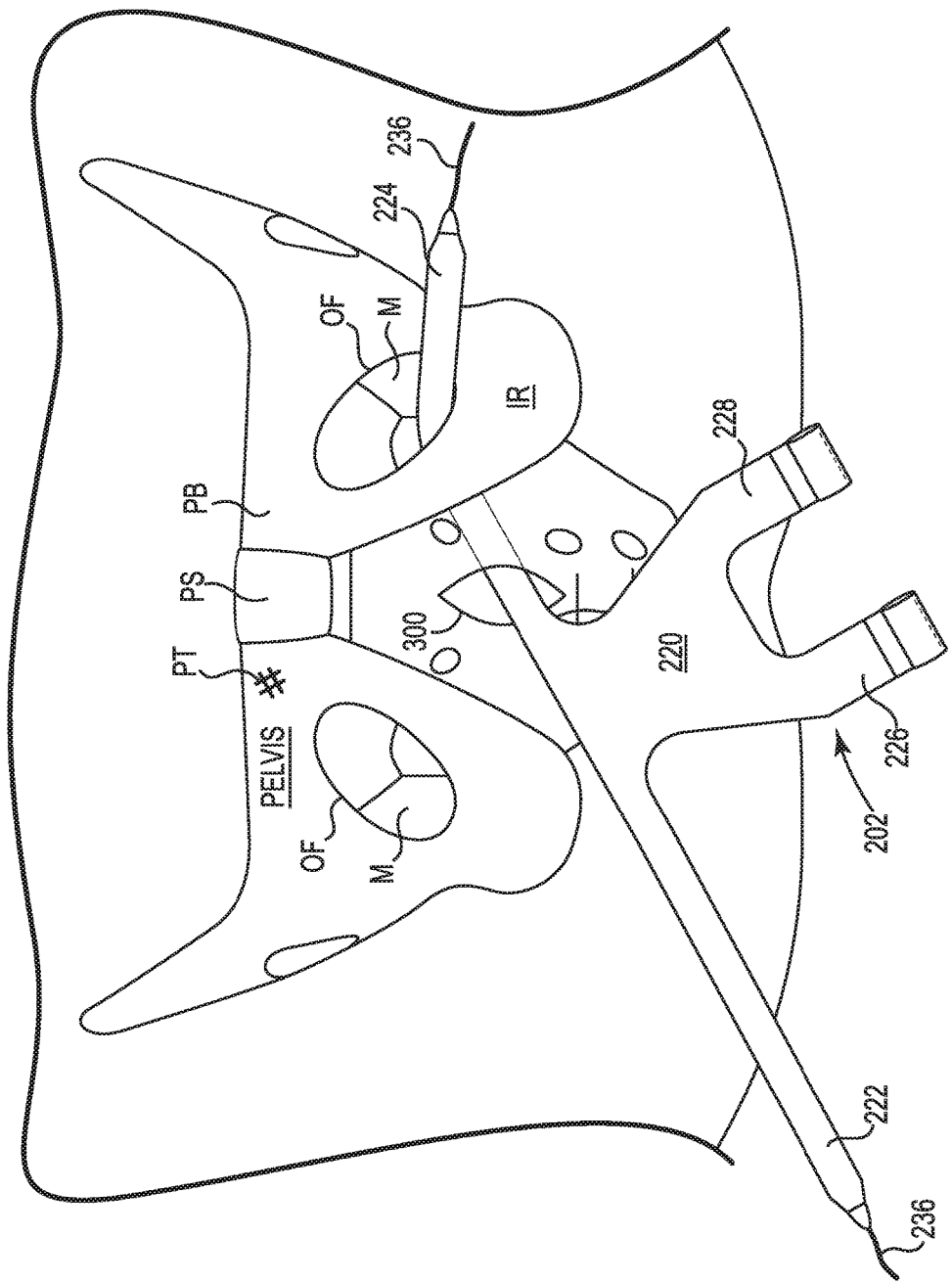

FIG. 14 is a schematic view of the lateral arm 224 inserted through the obturator foramen OF with the other portions of the support 202 extending out of the incision 300. The other lateral arm 222 of the support 202 is available outside of the patient's body for attachment to the distal end of the J-hook device 206 prior to its eventual insertion through the other obturator foramen.

Figure 15:
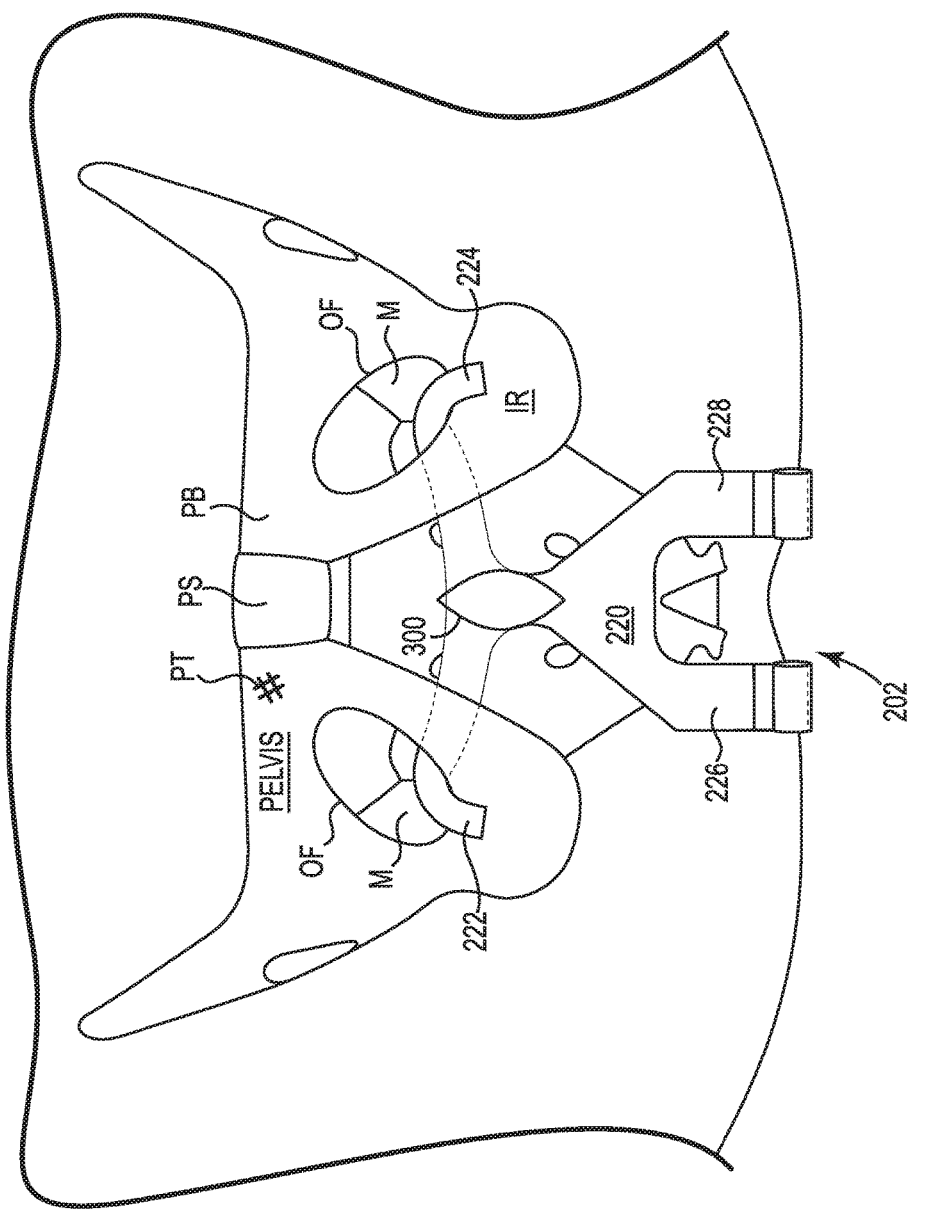

FIG. 15 is a schematic view of the first lateral arm 222 inserted through one of the obturator foramen OF and the second lateral arm 224 inserted through the second obturator foramen OF. The surgeon terminates or attaches the arms 222, 224 to the tissue of the patient to stabilize the lower portion of the support 202. The longitudinal arms 226, 228 of the support 202 extend outside of the incision 300 and are available for coupling with the brace 204 (FIG. 9).

Figure 16:
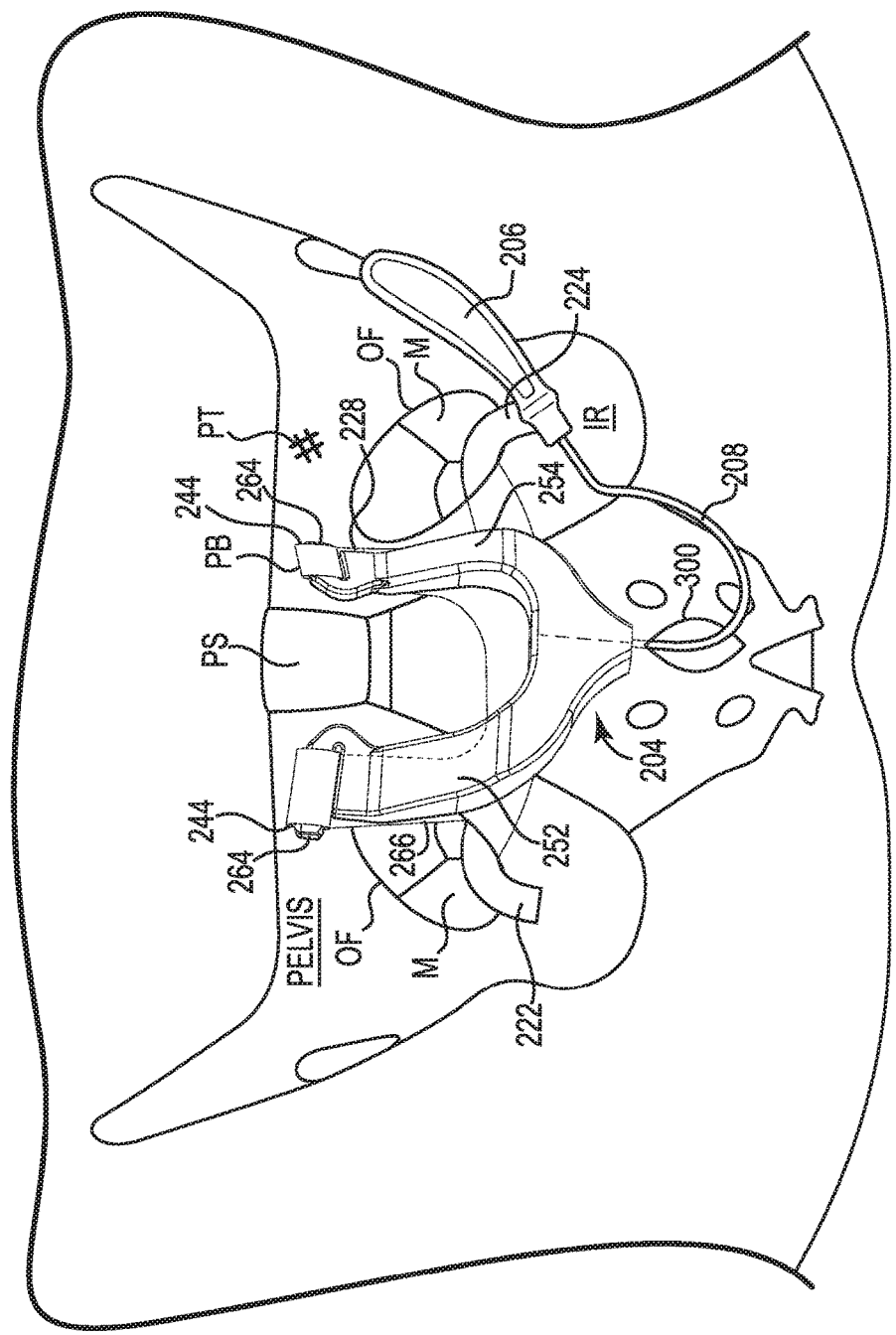

FIG. 16 is a schematic view of the male pelvis with each of the lateral arms 222, 224 implanted through one of the obturator foramen OF, and the brace 204 is engaged with the longitudinal arms 226, 228 of the support 202. The device 206 is attachable to the brace 204 for implantation of the longitudinal arms 226, 228. Each of the hangers 264 is inserted into one of the pockets 244 formed in the longitudinal arms 226, 228. Each of the posts 252, 254 of the brace 204 are individually inserted through the incision 300 and lifted to an anterior location of the pelvis on either side of the pubic symphysis PS. The surgeon may choose to employ a retractor (not shown) to expand the opening of the incision 300. In any regard, the brace 204 is attached to the pocket 244 of each of the arms 226, 226 of the support 202 and subsequently inserted through the incision 300.

The device 206 is attached to the brace 204 and projects outside of the incision 300. The device 206 provides a lever that allows the longitudinal arms 226, 228 to be lifted and positioned relative to the pubic bone and to also lift and displace tissue away from the pelvis.

Figure 17:
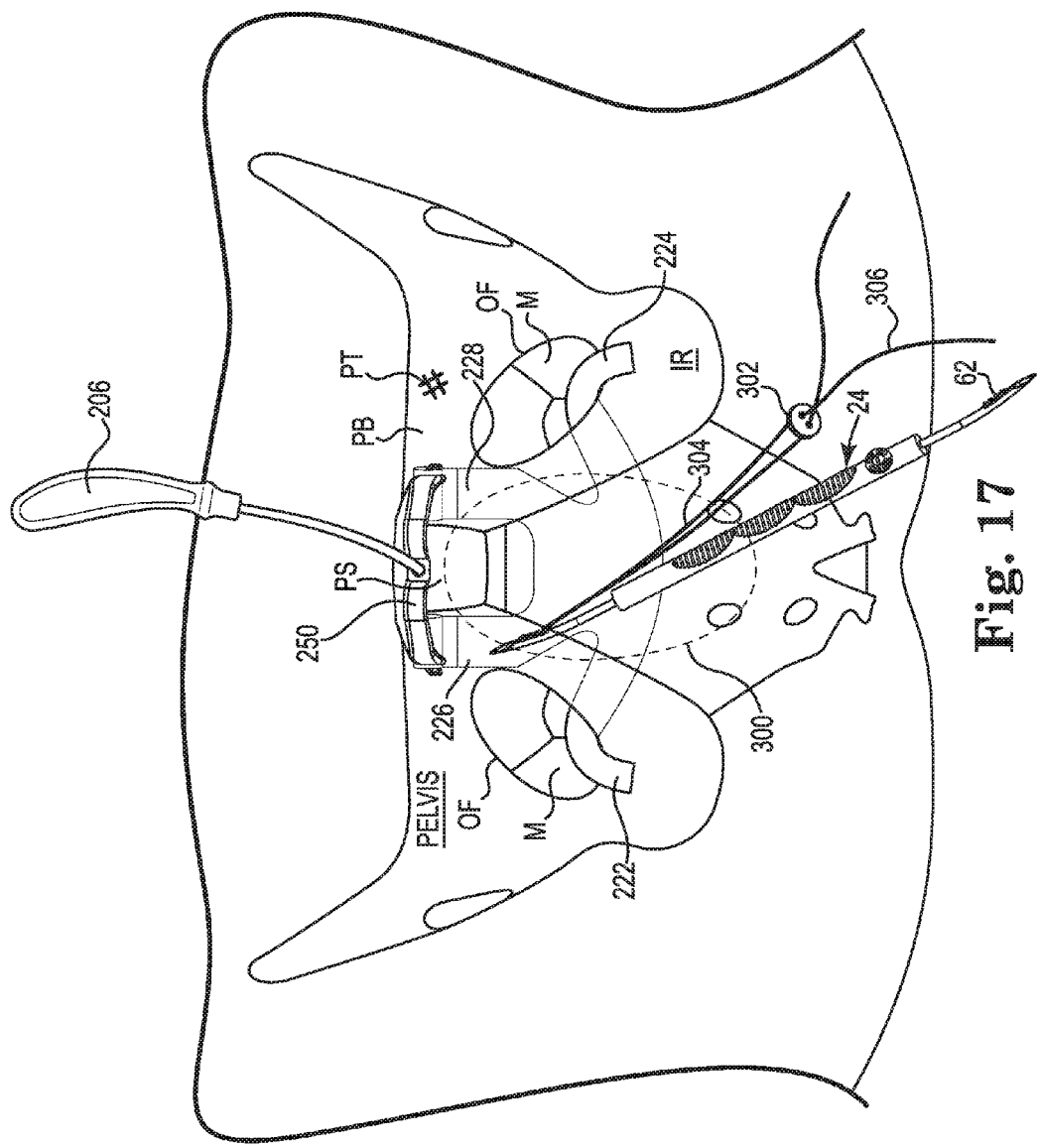

FIG. 17 is a schematic view of the longitudinal arms 226, 228 of the support 202 held in place on either side of the pubic symphysis PS by the device 206. The incision 300 is supported and expanded by a suitable retractor. In addition, when the device 206 is rotated upward, the base portion 250 of the brace 204 "opens" the incision 300 further. The upward rotation of the brace 204 lifts the posts 252, 254 away from the arms 226, 228 of the support 202. In this manner, the brace 204 has been employed as a lever by the surgeon to provide access to the longitudinal arms 226, 228 of the support 202. The introducer 24 is inserted into the incision 300 and toward the pelvis to place one of the anchors 22, 62 through the support 202 and into the periosteum tissue PT. The introducer 24 includes the sharp distal end that pierces through the support 202 and the periosteum tissue PT to slide the anchor 22 between the bone of the pelvis and the periosteum tissue PT. Removal of the introducer 24 back through the incision leaves the anchor 22 implanted in the periosteum tissue with a suture line 304 trailing out of the incision 300. The stopper 302 is delivered in a distal direction to hold the suture 304 and the anchor 22 in place against the periosteum tissue PT. The same process of rotating the brace 204 for access to the arms 226, 228 of the support 202 is employed on the contralateral side until each of the longitudinal arms 226, 228 is appropriately attached to the periosteum tissue PT by the anchors 22, 62. The order of the placement of the anchors 22 and 62 is for illustrative purposely; it is acceptable to reverse the order of the placement of the anchors 22 and 62.

Figure 18:
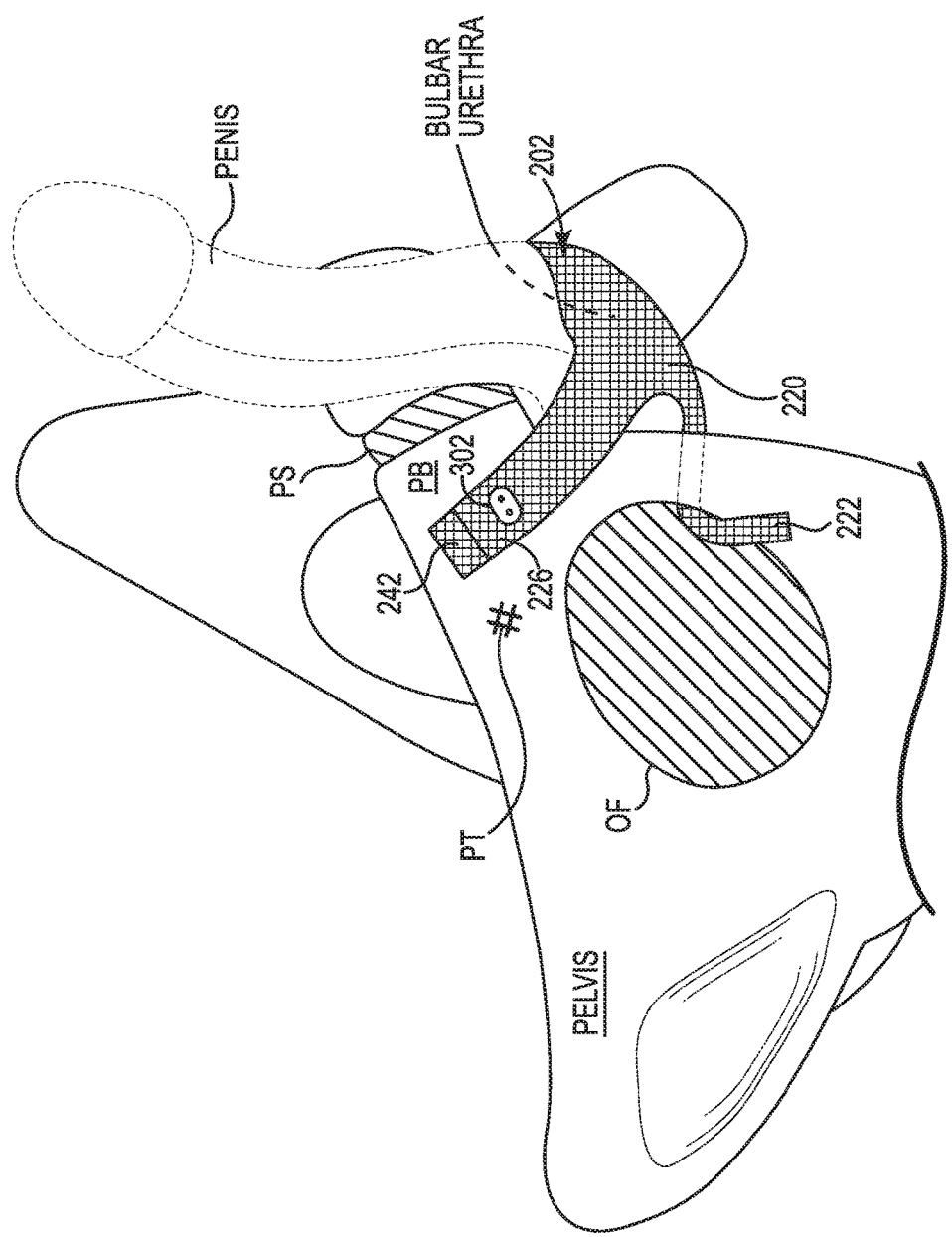

FIG. 18 is a schematic perspective view of the male pelvis with the support 202 elevating and compressing the bulbar urethra. Each of the lateral arms 222, 224 has been introduced through the obturator foramen and implanted as described above. Each of the longitudinal arms 226, 228 has been attached to the periosteum tissue PT and held in place by one of the anchors 22, 62 and the stopper 302. The upper end portion 242 of each the longitudinal arms 226, 228 may be removed by the surgeon (or left in place, depending upon surgeon preference). The incision 300 is closed and the support 202 is thus operatively implanted and connected to the tissue around the pelvis to support the urethra and treat male incontinence.

Figure 19:
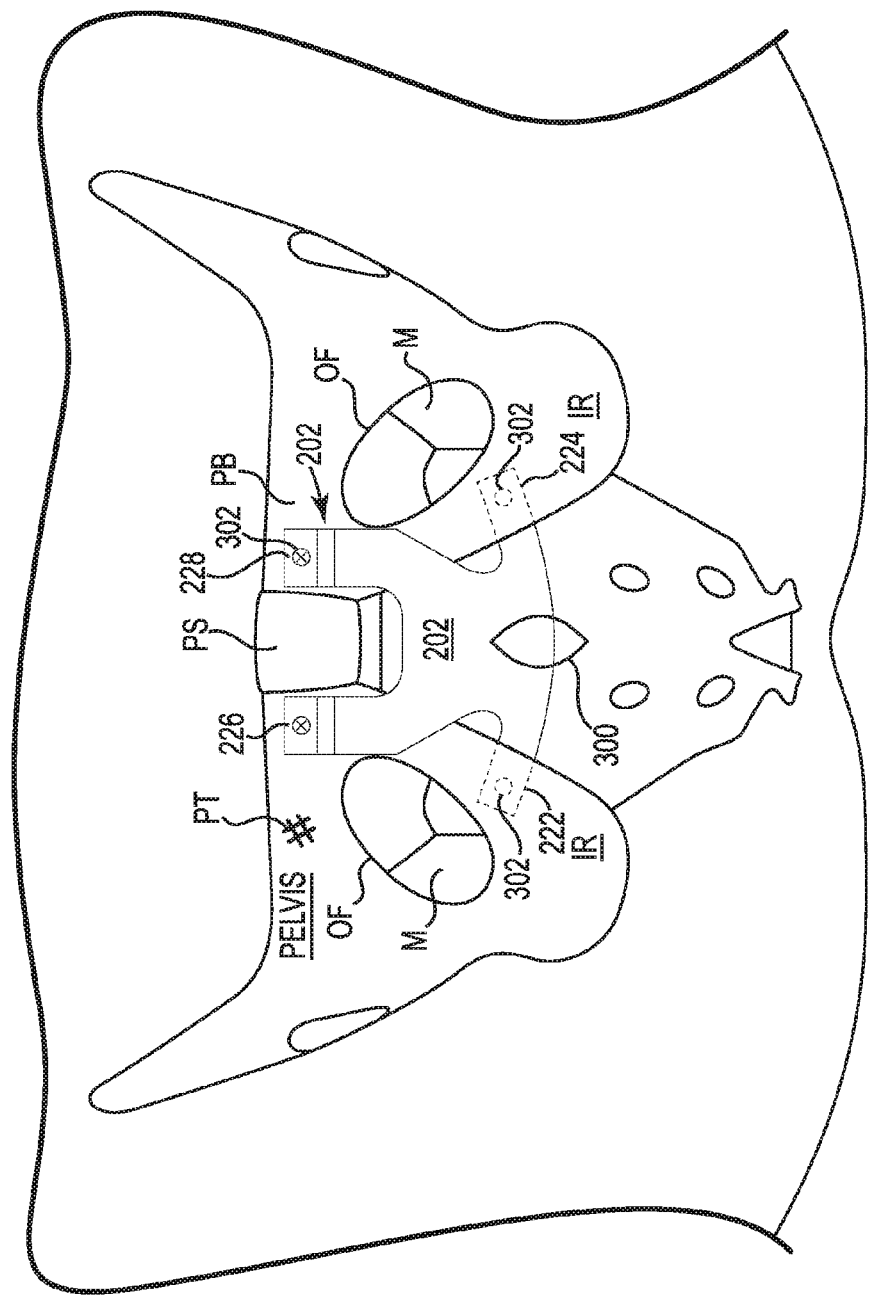

FIG. 19 is a schematic view of one embodiment of the support 202 implanted in a male patient. The longitudinal arms 226, 228 have been implanted in the patient and attached to the periosteum tissue with the anchors 22, 62 of the system 20 described above. In one embodiment, each of the lateral arms 222, 224 is inserted through the incision 300 and directed to a posterior location of the descending ischial ramus IR and connected to the periosteum tissue of the pelvis with one of the anchors 22, 62 of the system 20 described above (the anchors 22, 62 are posterior the support 202 and thus not in the view of FIG. 19). The stoppers 302 are anterior the support 202. In this manner, the entire support 202 is connected to the periosteum tissue PT of the male patient and the obturator foramen OF (and the membrane M covering the operator foramen OF) is not disturbed. The method of implanting the support 202 as illustrated in FIG. 19 provides for and allows a true single incision approach to the implantation of the support structure in treating male incontinence.

Embodiments provide for the fixation of a support in a male patient to treat urinary incontinence, where the implantation and the fixation are conducted through a true single (only one) incision site. The fixation is achieved without bone screws and the fixation is not attached to bone.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of medical devices as discussed herein. Therefore, it is intended that this invention is limited only by its claims and their equivalents.

What is claimed is:

1. A tool useful for implanting a support in treating urinary incontinence in a patient, the tool comprising:
   a hook connected to a handle, the hook having a curvature; and
   a brace attachable to the hook, the brace including:
      two posts extending from a base portion, the two posts including a first post that is spaced a distance apart from a second post, with a first hanger connected to the first post at a location opposite from the base portion and a second hanger connected to the second post at a location opposite from the base portion, where the base portion has a recess that is sized to receive a tip of the hook;
   wherein the first post has an inside edge and an outside edge, with the outside edge of the first post farther away from the second post than the inside edge of the first post is away from the second post;
   wherein the second post has an inside edge and an outside edge, with the outside edge of the second post farther away from the first post than the inside edge of the second post is away from the first post;
   wherein a first slot is formed in the first hanger through the outside edge of the first post and a second slot is formed in the second hanger through the outside edge of the second post.

2. The tool of claim 1, wherein the hook is a J-hook configured for accessing an obturator foramen of the patient.

3. The tool of claim 1, wherein the base portion is aligned on a base portion plane, the first post is disposed in a first plane, and the second post is disposed in a second plane;
   wherein the base portion plane is not co-planar with either of the first plane and the second plane, and the first plane is not co-planar with the second plane.

4. The tool of claim 1, wherein the first post and the first hanger have a curvature in a longitudinal direction.

5. The tool of claim 1, wherein the brace has a distal side adapted to be oriented toward the pelvis of the patient and a proximal side opposite of the distal side that is adapted to face away from the patient, and the base portion has a lateral curvature such that the distal side is concave and the proximal side is convex.

6. The tool of claim 1, wherein the first hanger is attached at the inside edge of the first post and the second hanger is attached at the inside edge of the second post.

7. The tool of claim 1, wherein the brace has a distal side adapted to be oriented toward the pelvis of the patient and a proximal side opposite of the distal side that is adapted to face away from the patient, and the brace has a complex curvature including a concave lateral curvature formed in the distal side of the base portion of the brace and a concave longitudinal curvature formed in the proximal side of the two posts of the brace.

8. A tool useful for implanting a support in treating urinary incontinence in a patient, the tool comprising:
   a brace including two posts extending from a base portion, the two posts including a first post that is spaced a distance apart from a second post, with the base portion aligned in a base portion plane, the first post disposed in a first plane, and the second post disposed in a second plane, where the base portion plane is not co-plan with either of the first plane and the second plane, and the first plane is not co-planar with the second plane, where a side of the base portion opposite from the first post and opposite from the second post includes a recess formed in the base portion; and
   a hook connected to a handle, where the hook has a first section attached to the handle, a second section that is curved to have a J-hook curvature configured for accessing an obturator foramen of the patient, and a third section including a tip;
   wherein the tip of the hook is removably insertable into the recess formed in the base portion.

9. The tool of claim 8, wherein a first slot is formed through an outside edge of the first post and a second slot is formed through an outside edge of the second post.

10. The tool of claim 8, wherein the brace has a complex curvature including a concave lateral curvature formed in the base portion of the brace and a concave longitudinal curvature formed in the first post and the second post of the brace.

11. The tool of claim 8, further comprising:
   a first hanger connected to the first post at a location opposite from the base portion and a second hanger connected to the second post at a location opposite from the base portion.

* * * * *